(12) United States Patent
McBurney et al.

(10) Patent No.: US 6,548,241 B1
(45) Date of Patent: Apr. 15, 2003

(54) STORAGE SOLUTION CONTAINING PHOTOSENSITIZER FOR INACTIVATION OF BIOLOGICAL CONTAMINANTS

(75) Inventors: Laura McBurney, Lakewood, CO (US); Raymond P. Goodrich, Jr., Denver, CO (US)

(73) Assignee: Gambro, Inc., Lakewood, CO (US)

( * ) Notice: Subject to any disclaimer, the term of this patent is extended or adjusted under 35 U.S.C. 154(b) by 0 days.

(21) Appl. No.: 09/725,426

(22) Filed: Nov. 28, 2000

(51) Int. Cl.⁷ .............................. A01N 1/02; C12N 5/08; A61K 31/33
(52) U.S. Cl. ........................... 435/2; 435/372; 574/183
(58) Field of Search ...................... 435/2, 372; 514/183

(56) References Cited

U.S. PATENT DOCUMENTS

| | | | |
|---|---|---|---|
| 2,786,014 A | 3/1957 | Tullis | 167/78 |
| 3,629,071 A | 12/1971 | Sekhar | 195/1.8 |
| 3,874,384 A | 4/1975 | Deindoerfer et al. | 128/272 |

(List continued on next page.)

FOREIGN PATENT DOCUMENTS

| | | | |
|---|---|---|---|
| CS | 275936 | * | 3/1992 |
| EP | 0 066 886 | | 6/1982 |
| EP | 0 196 515 A1 | | 3/1986 |
| EP | 0 590 514 A1 | | 4/1994 |
| EP | 0 679 398 A1 | | 11/1995 |
| EP | 0 510 185 B1 | | 12/1996 |
| EP | 0 754 461 A2 | | 1/1997 |
| FR | 2674753 | | 10/1992 |
| FR | 2715303 | | 7/1995 |
| GB | 2034463 A | | 4/1980 |
| JP | 08165245 | | 6/1996 |
| WO | WO 83/02328 | | 7/1983 |
| WO | WO 85/02116 | | 5/1985 |
| WO | WO 87/05468 | | 9/1987 |
| WO | WO 90/00059 | | 1/1990 |
| WO | WO 92/08348 | | 5/1992 |
| WO | WO 92/08349 | | 5/1992 |
| WO | WO 92/17173 | | 9/1992 |
| WO | WO 94/07499 | | 4/1994 |
| WO | WO 95/11028 | | 4/1995 |
| WO | WO 95/16348 | | 6/1995 |
| WO | WO 96/14741 | | 5/1996 |
| WO | WO 97/18844 | | 5/1997 |
| WO | WO 97/36581 | | 10/1997 |
| WO | WO 98/31219 A1 | | 7/1998 |
| WO | WO 98/41087 | | 9/1998 |
| WO | WO 98/51147 | | 11/1998 |
| WO | WO 98/56247 | | 12/1998 |
| WO | WO 00/11946 | | 3/2000 |
| WO | WO 01/28599 A1 | | 4/2001 |
| WO | WO 01/96340 A1 | | 12/2001 |

OTHER PUBLICATIONS

Chow, C.S. and Barton, J.K., "Recognition of G–U mismatches by tris(4,7–diphenyl–1, 0–phenanthroline)rhodium(III)," (1992) *Biochemistry* 31(24):5423–5429.

Goodrich, R.P. and Platz, M.S., "The design and development of selective, photoactivated drugs for sterilization of blood products," (1997) *Drugs of the Future* 22(2):159–171.

Joshi, P.C., "Comparison of the DNA–damaging property of photosensitized riboflavin via singlet oxygen ($^1O_2$) and superoxide radical ($O_2^-$) mechanisms," (1985) *Toxicology Letters* 26:211–217.

Kabuta, H. et al. (1978), "Inactivation of viruses by dyes and visible light," Kurume Igakkai Zasshi 39(11):1067–77 (1976).

Kobayashi et al. (1983), "The molecular mechanism of mutation. Photodynamic action of flavins on the RNA–synthesizing system," Chem. Abstracts 98(1), Abstracts No. 1200.

Korycka–Dahl, M. and Richardson, T., "Photodegradation of DNA with fluorescent light in the presence of riboflavin, and photoprotection by flavin triplet–state quenchers," (1980) *Biochimica et Biophysica Acta* 610:229–234.

Naseem, I. et al., "Effect of alkylated and intercalated DNA on the generation of superoxide anion by riboflavin," (1988) *Bioscience Reports* 8(5):485–492.

Cadet, J. et al., "Mechanisms and Products of Photosensitized Degradation of Nucleic Acids and Related Model Compounds," (1983) *Israel J. Chem.* 23:420–429.

Ennever, J.F. and Speck, W.T., "Short Communication. Photochemical Reactions of Riboflavin: Covalent Binding to DNA and to Poly (dA)•Poly (dT)," (1983) *Pediatr. Res.* 17:234–236.

Kale, H. et al. (1992), "Assessment of the genotoxic potential of riboflavin and lumiflavin; B. Effect of light," Mutation Res. 298:17–23.

Kuratomi K. and Kobayashi, Y., "Studies on the Interactions Between DNA and Flavins," (1977) *Biochemica et Biophysica Acta* 476:207–217.

Matthews, J.L. et al., "Photodynamic therapy of viral contaminants with potential for blood banking applications," (1988) *Transfusion* 28(1):81–83.

Moroff, G. et al. "Use of Photochemical Procedures to Inactivate Viruses in Platelet Suspensions," *American Red Cross* S15 p. 9S.

Neyndorff, H.C. et al., "Development of a model to demonstrate photosensitizer–mediated viral inactivation in blood," (1990) *Quadra Logic Technologies, Inc. and the Department of Microbiology, University of British Columbia* 485–489.

North, J. et al. (1993), "New Trends in Photobiology (Invited Review)," J. Photochem. Photobiol. B: Biol. 17:99–108.

(List continued on next page.)

Primary Examiner—Sandra E. Saucier
Assistant Examiner—Vera Afremova
(74) Attorney, Agent, or Firm—Edna M. O'Connori; Laura M. Butterfield; Peter B. Scull

(57) ABSTRACT

A platelet/additive solution comprising bicarbonate, citrate and glucose. Additionally, a platelet/additive and treatment solution comprising bicarbonate, citrate, glucose and a photosensitizer.

2 Claims, 21 Drawing Sheets

U.S. PATENT DOCUMENTS

| | | |
|---|---|---|
| 4,061,537 A | 12/1977 | Seiler et al. ................. 195/1.7 |
| 4,112,070 A | 9/1978 | Harmening ................. 424/101 |
| 4,267,269 A | 5/1981 | Grode et al. .................... 435/2 |
| 4,390,619 A | 6/1983 | Harmening-Pittiglio ........ 435/2 |
| 4,432,750 A | 2/1984 | Estep ............................ 604/4 |
| 4,572,899 A | 2/1986 | Walker et al. ............... 436/118 |
| 4,585,735 A | 4/1986 | Meryman et al. ............... 435/2 |
| 4,609,372 A | 9/1986 | Carmen et al. ............. 604/262 |
| 4,626,431 A | 12/1986 | Batchelor et al. ........... 424/101 |
| 4,675,185 A | 6/1987 | Kandler et al. ............. 424/101 |
| 4,695,460 A | 9/1987 | Holme ........................ 424/101 |
| 4,704,352 A | 11/1987 | Miripol et al. ................. 435/2 |
| 4,726,949 A | 2/1988 | Miripol et al. ............. 424/101 |
| 4,748,120 A | 5/1988 | Wiesehahn .................. 435/173 |
| 4,769,318 A | 9/1988 | Hamasaki et al. ............. 435/2 |
| RE32,874 E | 2/1989 | Rock et al. .................. 424/101 |
| 4,828,976 A | 5/1989 | Murphy .......................... 435/2 |
| 4,925,665 A | 5/1990 | Murphy ...................... 424/532 |
| 4,961,928 A | 10/1990 | Holme et al. ............... 424/533 |
| 4,992,363 A | 2/1991 | Murphy .......................... 435/2 |
| 4,994,367 A | 2/1991 | Bode et al. ..................... 435/2 |
| 4,999,375 A | 3/1991 | Bachynsky et al. ......... 514/455 |
| 5,011,695 A | 4/1991 | Dichtelmuller et al. ..... 424/529 |
| 5,041,078 A | 8/1991 | Matthews et al. ............. 604/4 |
| 5,120,649 A | 6/1992 | Horowitz et al. ........... 435/713 |
| 5,147,776 A | 9/1992 | Koener, Jr. ..................... 435/2 |
| 5,211,960 A | 5/1993 | Babior ........................ 424/534 |
| 5,232,844 A | 8/1993 | Horowitz et al. ........ 435/173.1 |
| 5,234,808 A | 8/1993 | Murphy .......................... 435/2 |
| 5,236,716 A | 8/1993 | Carmen et al. ............. 424/532 |
| 5,247,178 A | 9/1993 | Ury et al. .................... 250/438 |
| 5,248,506 A | 9/1993 | Holme et al. ............... 424/533 |
| 5,250,303 A | 10/1993 | Meryman et al. ........... 424/533 |
| 5,281,392 A | 1/1994 | Rubinstein ................... 422/28 |
| 5,288,605 A | 2/1994 | Lin et al. ..................... 435/902 |
| 5,290,221 A | 3/1994 | Wolf, Jr. et al. ................ 604/4 |
| 5,342,752 A | 8/1994 | Platz et al. ..................... 435/2 |
| 5,344,752 A | 9/1994 | Murphy .......................... 435/2 |
| 5,358,844 A | 10/1994 | Stossel et al. .................. 435/2 |
| 5,376,524 A | 12/1994 | Murphy et al. ................. 435/2 |
| 5,378,601 A | 1/1995 | Gepner-Puszkin ............. 435/2 |
| 5,418,130 A | 5/1995 | Platz et al. ..................... 435/2 |
| 5,459,030 A | 10/1995 | Lin et al. ........................ 435/2 |
| 5,466,573 A | 11/1995 | Murphy et al. ................. 435/2 |
| 5,474,891 A | 12/1995 | Murphy .......................... 435/2 |
| 5,482,828 A | 1/1996 | Lin et al. ........................ 435/2 |
| 5,487,971 A | 1/1996 | Holme et al. ................... 435/2 |
| 5,512,187 A | 4/1996 | Buchholz et al. ........... 210/767 |
| 5,516,629 A | 5/1996 | Park et al. ...................... 435/2 |
| 5,569,579 A | 10/1996 | Murphy .......................... 435/2 |
| 5,587,490 A | 12/1996 | Goodrich, Jr. et al. ...... 549/282 |
| 5,593,823 A | 1/1997 | Wollowitz et al. ............. 435/2 |
| 5,622,867 A | 4/1997 | Livesey et al. ............... 436/18 |
| 5,624,794 A | 4/1997 | Bitensky et al. ............... 435/2 |
| 5,656,154 A | 8/1997 | Meryman .................... 210/97 |
| 5,656,498 A | 8/1997 | Iijima et al. .................. 436/10 |
| 5,658,722 A | 8/1997 | Margolis-Nunno et al. ..... 435/2 |
| 5,691,132 A | 11/1997 | Wollowitz et al. ............. 435/2 |
| 5,709,992 A | 1/1998 | Rubinstein ..................... 435/2 |
| 5,712,085 A | 1/1998 | Wollowitz et al. .......... 465/148 |
| 5,736,313 A | 4/1998 | Spargo et al. .................. 435/2 |
| 5,753,428 A | 5/1998 | Yuasa et al. .................... 435/2 |
| 5,769,839 A | 6/1998 | Carmen et al. ............. 604/408 |
| 5,783,093 A | 7/1998 | Holme ........................ 210/767 |
| 5,789,150 A | 8/1998 | Margolis-Nunno et al. ..... 435/2 |
| 5,789,151 A | 8/1998 | Bitensky et al. ............... 435/2 |
| 5,789,601 A | 8/1998 | Park et al. ................... 549/283 |
| 5,798,238 A | 8/1998 | Goodrich, Jr. et al. ... 435/173.3 |
| 5,834,198 A | 11/1998 | Famulok et al. ............... 435/6 |
| 5,840,252 A | 11/1998 | Giertych ....................... 422/40 |
| 5,858,643 A | 1/1999 | Ben-Hur et al. ............... 435/2 |
| 5,869,701 A | 2/1999 | Park et al. ................... 549/283 |
| 5,871,900 A | 2/1999 | Wollowitz et al. ............. 435/2 |
| 5,876,676 A | 3/1999 | Stossel et al. ................ 422/12 |
| 5,899,874 A | 5/1999 | Jonsson ......................... 604/4 |
| 5,906,915 A | 5/1999 | Payrat et al. ................... 435/2 |
| 5,908,742 A | 6/1999 | Lin et al. ........................ 435/2 |
| 5,919,614 A | 7/1999 | Livesey et al. ................. 435/2 |
| 5,948,918 A | 9/1999 | Lin et al. .................... 549/403 |
| 5,955,256 A | 9/1999 | Sowemimo-Coker et al. . 435/2 |
| 5,955,257 A | 9/1999 | Burger et al. .................. 435/2 |
| 5,965,349 A | 10/1999 | Lin et al. ........................ 435/2 |
| 6,004,741 A | 12/1999 | Wollowitz et al. ............. 435/2 |
| 6,017,691 A | 1/2000 | Wollowitz et al. ............. 435/2 |
| 6,020,333 A | 2/2000 | Berque ........................ 514/251 |
| 6,060,233 A | 5/2000 | Wiggins ......................... 435/2 |
| 6,063,624 A | 5/2000 | Kandler et al. ............. 435/372 |
| 6,077,659 A | 6/2000 | Ben-Hur et al. ............... 435/2 |

OTHER PUBLICATIONS

Peak, J.G. et al., "DNA Breakage Caused by 334–nm Ultraviolet Light is Enhanced by Naturally Occurring Nucleic Acid Components and Nucleotide Coenszymes," (1984) *Photochemistry and Photobiology* 39(5):713–716.

Piette, J. et al., "Alteration of Guanine Residues During Proflaving Mediated Photosensitization of DNA," (1981) *Photochemistry and Photobiology* 33:325–333.

Piette, J. et al., "Production of Breaks in Single– and Double–Standard Forms of Bacteriophage φX174 DNA by Proflavine and Light Treatment," (1979) *Photochemistry and Photobiology* 30:369–378.

Speck, W.T. et al., "Further Observations on the Photooxidation of DNA in the Presence of Riboflavin," (1976) *Biochimica et Biphysica Acta* 435:39–44.

Tsugita, A. et al., "Photosensitized inactivation of ribonucleic acids in the presence of riboflavin," (1965) *Biochim. Biophys. Acta* 103:360–363.

\* cited by examiner

STORAGE SOLUTION CONTAINING PHOTOSENSITIZER FOR INACTIVATION OF BIOLOGICAL CONTAMINANTS

FIELD OF INVENTION

This invention relates to blood component storage solutions and more particularly to blood component storage solutions containing a photosensitizer for viral inactivation.

BACKGROUND

Contamination of blood supplies with infectious microorganisms such as HIV, hepatitis and other viruses and bacteria presents a serious health hazard for those who must receive transfusions of whole blood or administration of various blood components such as platelets, red cells, blood plasma, Factor VIII, plasminogen, fibronectin, antithrombin III, cryoprecipitate, human plasma protein fraction, albumin, immune serum globulin, prothrombin complex plasma growth hormones, and other components isolated from blood. Blood screening procedures may miss contaminants, and sterilization procedures which do not damage cellular blood components but effectively inactivate all infectious viruses and other microorganisms have not heretofore been available.

Solvent detergent methods of blood component decontamination work by dissolving phospholipid membranes surrounding viruses such as HIV, and do not damage protein components of blood; however, if blood cells are present, such methods cannot be used because of damage to cell membranes.

The use of photosensitizers, compounds which absorb light of a defined wavelength and transfer the absorbed energy to an energy acceptor, has been proposed for blood component sterilization. For example, European Patent application 196,515 published Oct. 8, 1986, suggests the use of non-endogenous photosensitizers such as porphyrins, psoralens, acridine, toluidines, flavine (acriflavine hydrochloride), phenothiazine derivatives, and dyes such as neutral red, and methylene blue, as blood additives. Protoporphyrin, which occurs naturally within the body, can be metabolized to form a photosensitizer; however, its usefulness is limited in that it degrades desired biological activities of proteins. Chlorpromazine, is also exemplified as one such photosensitizer; however its usefulness is limited by the fact that it should be removed from any fluid administered to a patient after the decontamination procedure because it has a sedative effect.

Goodrich, R. P., et al. (1997), "The Design and Development of Selective, Photoactivated Drugs for Sterilization of Blood Products," Drugs of the Future 22:159–171 provides a review of some photosensitizers including psoralens, and some of the issues of importance in choosing photosensitizers for decontamination of blood products. The use of texaphyrins for DNA photocleavage is described in U.S. Pat. No. 5,607,924 issued Mar. 4, 1997 and U.S. Pat. No. 5,714,328 issued Feb. 3, 1998 to Magda et al. The use of sapphyrins for viral deactivation is described in U.S. Pat. No. 5,041,078 issued Aug. 20, 1991 to Matthews, et al. Inactivation of extracellular enveloped viruses in blood and blood components by Phenthiazin-5-ium dyes plus light is described in U.S. Pat. No. 5,545,516 issued Aug. 13, 1996 to Wagner. The use of porphyrins, hematoporphyrins, and merocyanine dyes as photosensitizing agents for eradicating infectious contaminants such as viruses and protozoa from body tissues such as body fluids is disclosed in U.S. Pat. No. 4,915,683 issued Apr. 10, 1990 and related U.S. Pat. No. 5,304,113 issued Apr. 19, 1994 to Sieber et al. The mechanism of action of such photosensitizers is described as involving preferential binding to domains in lipid bilayers, e.g. on enveloped viruses and some virus-infected cells. Photoexcitation of membrane-bound agent molecules leads to the formation of reactive oxygen species such as singlet oxygen which causes lipid peroxidation. A problem with the use of such photosensitizers is that they attack cell membranes of desirable components of fluids to be decontaminated, such as red blood cells, and the singlet oxygen also attacks desired protein components of fluids being treated. U.S. Pat. No. 4,727,027 issued Feb. 23, 1988 to Wiesehahn, G. P., et al. discloses the use of furocoumarins including psoralen and derivatives for decontamination of blood and blood products, but teaches that steps must be taken to reduce the availability of dissolved oxygen and other reactive species in order to inhibit denaturation of biologically active proteins. Photoinactivation of viral and bacterial blood contaminants using halogenated coumarins is described in U.S. Pat. No. 5,516,629 issued May 14, 1996 to Park, et al. U.S. Pat. No. 5,587,490 issued Dec. 24, 1996 to Goodrich Jr., R. P., et al. and U.S. Pat. No. 5,418,130 to Platz, et al. disclose the use of substituted psoralens for inactivation of viral and bacterial blood contaminants. The latter patent also teaches the necessity of controlling free radical damage to other blood components. U.S. Pat. No. 5,654,443 issued Aug. 5, 1997 to Wollowitz et al. teaches new psoralen compositions used for photodecontamination of blood. U.S. Pat. No. 5,709,991 issued Jan. 20, 1998 to Lin et al. teaches the use of psoralen for photodecontamination of platelet preparations and removal of psoralen afterward. U.S. Pat. No. 5,120,649 issued Jun. 9, 1992 and related U.S. Pat. No. 5,232,844 issued Aug. 3, 1993 to Horowitz, et al., also disclose the need for the use of "quenchers" in combination with photosensitizers which attack lipid membranes, and U.S. Pat. No. 5,360,734 issued Nov. 1, 1994 to Chapman et al. also addresses this problem of prevention of damage to other blood components.

Photosensitizers which attack nucleic acids are known to the art. U.S. Pat. No. 5,342,752 issued Aug. 30, 1994 to Platz et al. discloses the use of compounds based on acridine dyes to reduce parasitic contamination in blood matter comprising red blood cells, platelets, and blood plasma protein fractions. These materials, although of fairly low toxicity, do have some toxicity e.g. to red blood cells. U.S. Pat. No. 5,798,238 to Goodrich, Jr., et al., discloses the use of quinolone and quinolone compounds for inactivation of viral and bacterial contaminants.

Binding of DNA with photoactive agents has been exploited in processes to reduce lymphocytic populations in blood as taught in U.S. Pat. No. 4,612,007 issued Sep. 16, 1986 and related U.S. Pat. No. 4,683,889 issued Aug. 4, 1987 to Edelson.

Riboflavin (7,8-dimethyl-10-ribityl isoalloxazine) has been reported to attack nucleic acids. Photoalteration of nucleic acid in the presence of riboflavin is discussed in Tsugita, A, et al. (1965), "Photosensitized inactivation of ribonucleic acids in the presence of riboflavin," Biochimica et Biophysica Acta 103:360–363; and Speck, W. T. et al. (1976), "Further Observations on the Photooxidation of DNA in the Presence of Riboflavin," Biochimica et Biophysica Acta 435:39–44. Binding of lumiflavin (7,8,10-trimethylisoalloxazine) to DNA is discussed in Kuratomi, K., et al. (1977), "Studies on the Interactions between DNA and Flavins," Biochimica et Biophysica Acta 476:207–217. Hoffmann, M. E., et al. (1979), "DNA Strand Breaks in Mammalian Cells Exposed to Light in the Presence of Riboflavin and Tryptophan," Photochemistry and Photobiology 29:299–303 describes the use of riboflavin and tryptophan to induce breaks in DNA of mammalian cells after exposure to visible fluorescent light or near-ultraviolet light. The article states that these effects did not occur if either riboflavin or tryptophan was omitted from the medium. DNA strand breaks upon exposure to proflavine and light are reported in Piette, J. et al. (1979), "Production of Breaks in Single- and Double-Stranded Forms of Bacteriophage ΦX174 DNA by Proflavine and Light Treatment," Photochemistry and Photobiology 30:369–378, and alteration of guanine residues during proflavine-mediated photosensitization of DNA is discussed in Piette, J., et al. (1981), "Alteration of Guanine Residues during Proflavine Mediated Photosensitization of DNA," Photochemistry and Photobiology 33:325–333.

J. Cadet, et al. (1983), "Mechanisms and Products of Photosensitized Degradation of Nucleic Acids and Related Model Compounds," Israel J. Chem. 23:420–429, discusses the mechanism of action by production of singlet oxygen of rose bengal, methylene blue, thionine and other dyes, compared with mechanisms not involving production of singlet oxygen by which nucleic acid attack by flavin or pteron derivatives proceeds. Riboflavin is exemplified in this disclosure as having the ability to degrade nucleic acids. Korycka-Dahl, M., et al. (1980), "Photodegradation of DNA with Fluorescent Light in the Presence of Riboflavin, and Photoprotection by Flavin Triplet-State Quenchers," Biochimica et Biophysica Acta 610:229–234 also discloses that active oxygen species are not directly involved in DNA scission by riboflavin. Peak, J. G., et al. (1984), "DNA Breakage Caused by 334-nm Ultraviolet Light is Enhanced by Naturally Occurring Nucleic Acid Components and Nucleotide Coenzymes," Photochemistry and Photobiology 39:713–716 further explores the mechanism of action of riboflavin and other photosensitizers. However, no suggestion is made that such photosensitizers be used for decontamination of medical fluids.

Apparatuses for decontamination of blood have been described in U.S. Pat. No. 5,290,221 issued Mar. 1, 1994 to Wolfe, Jr., et al. and U.S. Pat. No. 5,536,238 issued Jul. 16, 1996 to Bischof. U.S. Pat. No. 5,290,221 discloses the irradiation of fluid in a relatively narrow, arcuate gap. U.S. Pat. No. 5,536,238 discloses devices utilizing optical fibers extending into a filtration medium. Both patents recommend as photosensitizers benzoporphryin derivatives which have an affinity for cell walls. The PCT publication WO 80/04930 which is incorporated by reference herein and which claims priority from U.S. patent application Ser. No. 09/119,666, filed Jul. 21, 1998, and U.S. patent application Ser. No. 09/357,188, filed Jul. 20, 1999, discloses the use of riboflavin as a photosensitizer.

All publications referred to herein are hereby incorporated by reference to the extent not inconsistent herewith.

SUMMARY

The instant invention relates to the addition of a photosensitizer to treat fluid or other material to inactivate at least some of the microorganisms and white cells which may be present therein.

One mechanism by which these photosensitizers may inactivate microorganisms is by interfering with nucleic acids, so as to prevent replication of the nucleic acid.

As used herein, the term "inactivation of a microorganism" means totally or partially preventing the microorganism from replicating, either by killing the microorganism or otherwise interfering with its ability to reproduce.

Microorganisms include viruses (both extracellular and intracellular), bacteria, bacteriophages, fungi, blood-transmitted parasites, and protozoa. Exemplary viruses include acquired immunodeficiency (HIV) virus, hepatitis A, B and C viruses, sinbis virus, cytomegalovirus, vesicular stomatitis virus, herpes simplex viruses, e.g. types I and II, human T-lymphotropic retroviruses, HTLV-III, lymphadenopathy virus LAV/IDAV, parvovirus, transfusion-transmitted (TT) virus, Epstein-Barr virus, and others known to the art. Bacteriophages include ΦX174, Φ6, λ, R17, $T_4$, and $T_2$. Exemplary bacteria include *P. aeruginosa, S. aureus, S. epidermidis, L. monocytogenes, E. coli, K. pneumonia* and *S. marcescens*.

Inactivation of white blood cells may be desirable when suppression of immune or autoimmune response is desired, e.g., in processes involving transfusion of red cells, platelets or plasma when donor white blood cells may be present.

Platelet additive solutions comprising endogenous photosensitizers and endogenously-based derivative photosensitizers are provided herein. Platelet additive solutions known to the art may be used for this purpose and include those disclosed in U.S. Pat. Nos. 5,908,742; 5,482,828; 5,569,579; 5,236,716; 5,089,146; and 5,459,030. Such platelet additive solutions may contain physiological saline solution, buffer, and other components including magnesium chloride and sodium gluconate. The pH of such solutions is preferably between about 7.0 and 8.0. These solutions are useful as carriers for platelet concentrates to allow maintenance of cell quality and metabolism during storage, reduce plasma content and extend storage life. The photosensitizer may be present in such solutions at any desired concentration from about 1 $\mu$M to the solubility of the photosensitizer in the solution, and preferably between about 8 $\mu$M and about 50 $\mu$M, more preferably about 10 $\mu$M. One platelet additive solution comprises sodium acetate, sodium chloride, sodium gluconate, 1.5 mM magnesium chloride, 1 mM sodium phosphate 14 $\mu$M 7,8-dimethyl-10-ribityl-isoalloxazine and preferably also 6 mM ascorbate.

In the preferred embodiment, a novel rather than a known platelet solution is used and such novel platelet additive solution has a pH between about 7.0 and 8.0 and comprises 63–95 mM of bicarbonate, 33–52 mM of glucose, 5.1–8.8 mM of citrate, and a preferred endogenous photosensitizer as defined below.

Materials which may be treated and stored using the solutions of this invention include any materials which are adequately permeable to photoradiation to provide sufficient light to achieve viral inactivation, or which can be suspended or dissolved in fluids which have such permeability to photoradiation. Examples of such materials are whole blood and aqueous compositions containing biologically active proteins derived from blood or blood constituents. Packed red cells, platelets and plasma (fresh or fresh frozen plasma) are exemplary of such blood constituents. In the preferred embodiment, platelets are treated and stored using the preferred solution of this invention. In addition, therapeutic protein compositions containing proteins derived from blood, such as fluids containing biologically active protein useful in the treatment of medical disorders, e.g. factor VIII, Von Willebrand factor, factor IX, factor X, factor XI, Hageman factor, prothrombin, anti-thrombin III, fibronectin, plasminogen, plasma protein fraction, immune serum globulin, modified immune globulin, albumin, plasma growth hormone, somatomedin, plasminogen streptokinase complex, ceruloplasmin, transferrin, haptoglobin, antitrypsin and prekallikrein may be treated by the decontamination methods of this invention. Other fluids which could benefit from the treatment of this invention are peritoneal solutions used for peritoneal dialysis which are sometimes contaminated during connection, leading to peritoneal infections.

The term "biologically active" means capable of effecting a change in a living organism or component thereof. "Biologically active" with respect to "biologically active protein" as referred to herein does not refer to proteins which are part of the microorganisms being inactivated. Similarly, "non-toxic" with respect to the photosensitizers means low or no toxicity to humans and other mammals, and does not mean non-toxic to the microorganisms being inactivated. "Substantial destruction" of biological activity means at least as much destruction as is caused by porphyrin and porphyrin derivatives, metabolites and precursors which are known to have a damaging effect on biologically active proteins and cells of humans and mammals. Similarly, "substantially non-toxic" means less toxic than porphyrin, porphyrin derivatives, metabolites and precursors that are known for blood sterilization.

The term "blood product" as used herein includes blood constituents and therapeutic protein compositions containing proteins derived from blood as defined above. Fluids containing biologically active proteins other than those derived from blood may also be treated by the methods of this invention.

The endogenous photosensitizers and endogenously-based photosensitizer derivatives used in this invention do not substantially destroy the biological activity of fluid components other than microorganisms. As much biological activity of these components as possible is retained, although in certain instances, when the methods are optimized, some loss of biological activity, e.g., denaturization of protein components, must be balanced against effective decontamination of the fluid. So long as fluid components retain sufficient biological activity to be useful for their intended or natural purposes, their biological activities are not considered to be "substantially destroyed."

The photosensitizers useful in this invention include any photosensitizers known to the art to be useful for inactivating microorganisms. A "photosensitizer" is defined as any compound which absorbs radiation of one or more defined wavelengths and subsequently utilizes the absorbed energy to carry out a chemical process. Examples of such photosensitizers include porphyrins, psoralens, dyes such as neutral red, methylene blue, acridine, toluidines, flavine (acriflavine hydrochloride) and phenothiazine derivatives, coumarins, quinolones, quinones, and anthroquinones. Photosensitizers of this invention may include compounds which preferentially adsorb to nucleic acids, thus focusing their photodynamic effect upon microorganisms and viruses with little or no effect upon accompanying cells or proteins. Other photosensitizers are also useful in this invention, such as those using singlet oxygen-dependent mechanisms. Most preferred are endogenous photosensitizers. The term "endogenous" means naturally found in a human or mammalian body, either as a result of synthesis by the body or because of ingestion as an essential foodstuff (e.g. vitamins) or formation of metabolites and/or byproducts in vivo. Examples of such endogenous photosensitizers are alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (ravine adenine dinucleotide [FAD]), alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations. The term "alloxazine" includes isoalloxazines. Endogenously-based derivative photosensitizers include synthetically derived analogs and homologs of endogenous photosensitizers which may have or lack lower (1–5) alkyl or halogen substituents of the photosensitizers from which they are derived, and which preserve the function and substantial non-toxicity thereof When endogenous photosensitizers are used, particularly when such photosensitizers are not inherently toxic or do not yield toxic photoproducts after photoradiation, no removal or purification step is required after decontamination, and treated product can be directly returned to a patient's body or administered to a patient in need of its therapeutic effect. Preferred endogenous photosensitizers are:

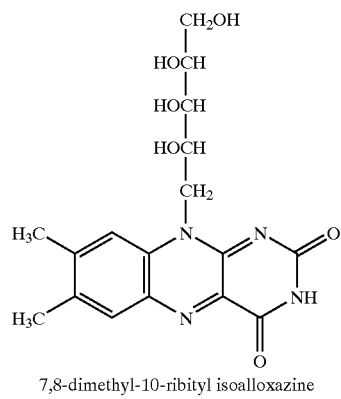
7,8-dimethyl-10-ribityl isoalloxazine

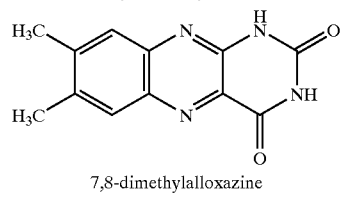
7,8-dimethylalloxazine

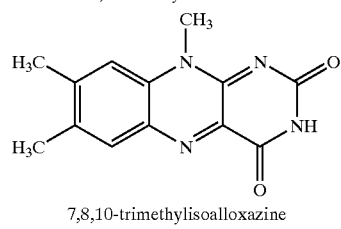
7,8,10-trimethylisoalloxazine

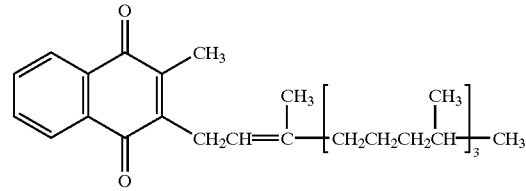
VITAMIN K1

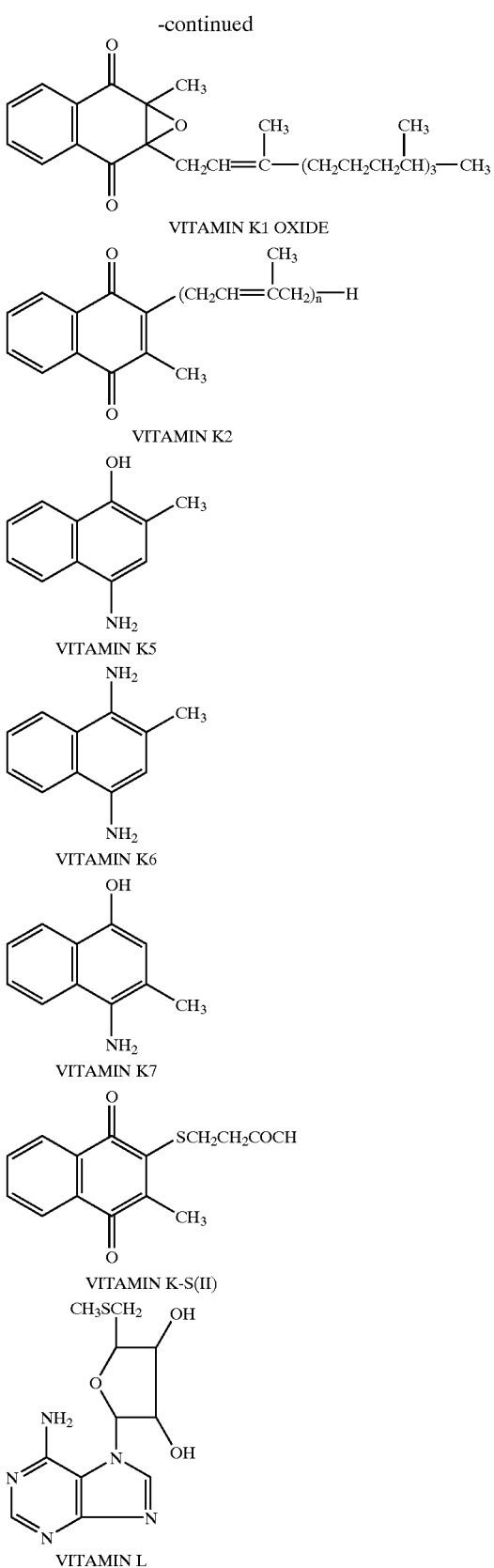

VITAMIN K1 OXIDE
VITAMIN K2
VITAMIN K5
VITAMIN K6
VITAMIN K7
VITAMIN K-S(II)
VITAMIN L

The photosensitizer of this invention is mixed with the material to be decontaminated. Mixing may be done by simply adding the photosensitizer in dry or aqueous form or the solution of this invention containing the photosensitizer to a fluid to be decontaminated. The material to be decontaminated to which photosensitizer has been added can be flowed past a photoradiation source, and the flow of the material generally provides sufficient turbulence to distribute the photosensitizer throughout the fluid to be decontaminated. Alternatively, the fluid and photosensitizer can be placed in a photopermeable container and irradiated in batch mode, preferably while agitating the container to fully distribute the photosensitizer and expose all the fluid to the radiation.

The amount of photosensitizer to be mixed with the fluid will be an amount sufficient to adequately inactivate microorganisms therein, but less than a toxic (to humans or other mammals) or insoluble amount. As taught herein, optimal concentrations for desired photosensitizers may be readily determined by those skilled in the art without undue experimentation. Preferably the photosensitizer is used in a concentration of at least about 1 $\mu$M up to the solubility of the photosensitizer in the fluid, and preferably about 10 $\mu$M. For 7,8 dimethyl-10-ribityl isoalloxazine a concentration range between about 1 $\mu$M and about 160 $\mu$M is preferred, preferably about 8 $\mu$M–50 $\mu$M.

The fluid containing the photosensitizer is exposed to photoradiation of the appropriate wavelength to activate the photosensitizer, using an amount of photoradiation sufficient to activate the photosensitizer as described above, but less than that which would cause non-specific damage to the biological components or substantially interfere with biological activity of other proteins present in the fluid. The wavelength used will depend on the photosensitizer selected, as is known to the art or readily determinable without undue experimentation following the teachings hereof. Preferably the light source is a fluorescent or luminescent source providing light of about 300 nm to about 700 nm, and more preferably about 340 nm to about 650 nm of radiation. Wavelengths in the ultraviolet to visible range are useful in this invention. The light source or sources may provide light in the visible range, light in the ultraviolet range, or a mixture of light in the visible and ultraviolet ranges.

The activated photosensitizer is capable of inactivating the microorganisms present, such as by interfering to prevent their replication. Specificity of action of the photosensitizer is conferred by the close proximity of the photosensitizer to the nucleic acid of the microorganism and this may result from binding of the photosensitizer to the nucleic acid. "Nucleic acid" includes ribonucleic acid (RNA) and deoxyribonucleic acid (DNA). Other photosensitizers may act by binding to cell membranes or by other mechanisms. The photosensitizer may also be targeted to the microorganism to be inactivated by covalently coupling to an antibody, preferably a specific monoclonal antibody to the microorganism.

The fluid containing the photosensitizer may be irradiated in a photopermeable container. The term "container" refers to a closed or open space, which may be made of rigid or flexible material, e.g., may be a bag or box or trough. It may be closed or open at the top and may have openings at both ends, e.g., may be a tube or tubing, to allow for flow-through of fluid therein. A cuvette has been used to exemplify one embodiment of the invention involving a flow-through system. Collection bags, such as those used with the Trima™ Spectra™ and apheresis systems of Cobe Laboratories, Inc., and permeable bags suitable for containing fluid have been used to exemplify another embodiment involving batchwise treatment of the fluid.

The term "photopermeable" means the material of the container is adequately transparent to photoradiation of the proper wavelength for activating the photosensitizer. In the flow-through system, the container has a depth (dimension measured in the direction of the radiation from the photoradiation source) sufficient to allow photoradiation to adequately penetrate the container to contact photosensitizer molecules at all distances from the light source and ensure inactivation of microorganisms in the fluid to be decontaminated, and a length (dimension in the direction of fluid flow) sufficient to ensure a sufficient exposure time of the fluid to the photoradiation. The materials for making such containers, depths and lengths of containers may be easily determined by those skilled in the art without undue experimentation following the teachings hereof, and together with the flow rate of fluid through the container, the intensity of the photoradiation and the absorptivities of the fluid components, e.g., plasma, platelets, red blood cells, will determine the amount of time the fluid needs to be exposed to photoradiation. For 7,8-dimethyl-10-ribityl isoalloxazine, a preferred amount of radiation is between about 1 $J/cm^2$ to 200 $J/cm^2$.

The fluid to be treated also may be placed in a photopermeable container which is agitated and exposed to photoradiation for a time sufficient to substantially inactivate the microorganisms. The photopermeable container is preferably a blood bag made of transparent or semitransparent plastic, and the agitating means is preferably a shaker table. The photosensitizer may be added to the container in dry form as a powder, tablet, capsule or pill or in liquid form and the container agitated to mix the photosensitizer with the fluid and to adequately expose all the fluid to the photoradiation to ensure inactivation of microorganisms. In the preferred embodiment, the photosensitizer is combined with the other constituents of the additive solution and such additive solution containing photosensitizer is added to the fluid to be treated. It is also contemplated that exposure of the fluid to photoradiation can also occur without agitation of the photopermeable container or that such agitation can occur prior to exposure.

The photosensitizer may be added to the photopermeable container before sterilization of such container or after sterilization. When the preferred additive solution containing photosensitizer is used, it is preferred that the glucose and photosensitizer mixture be separated from the citrate and bicarbonate mixture during sterilization to prevent degradation of the glucose and photosensitizer. More specifically, the glucose/photosensitizer mixture should be sterilized at a lower pH than that of the citrate/bicarbonate mixture.

This invention also comprises fluids comprising biologically active protein, blood or blood constituents and also containing endogenous photosensitizer, or endogenously based derivative photosensitizer, and an additive solution. The fluid may also contain inactivated microorganisms.

Any means for adding the photosensitizer or the additive solution containing photosensitizer to the fluid to be decontaminated and for placing the fluid in the photopermeable container known to the art may be used, such means typically including flow conduits, ports, reservoirs, valves, and the like. It may be desirable that the system include means such as pumps or adjustable valves for controlling the flow of the photosensitizer into the fluid to be decontaminated so that its concentration may be controlled at effective levels as described above. The photosensitizer can be added to the fluid to be decontaminated in a pre-mixed aqueous solution, e.g., in water or storage buffer solution. Preferably the photosensitizer is added to the fluid to be decontaminated in aqueous form, but it could also be added as a dry medium in powder, pill, tablet or capsule form.

In one embodiment the fluid is placed in a photopermeable container such as a blood bag, e.g. used with the apheresis system described in U.S. Pat. No. 5,653,887, and agitated while exposing to photoradiation. Suitable bags include collection bags as described herein. Collection bags used in the Spectra™ system or Trima™ apheresis system of Cobe Laboratories, Inc. are especially suitable. Shaker tables are known to the art, e.g. as described in U.S. Pat. No. 4,880,788. The bag is equipped with at least one port for adding fluid thereto. In one embodiment an additive solution containing the photosensitizer, preferably 7,8-dimethyl-10 ribityl-isoalloxazine, is added to the fluid-filled bag in liquid form. The bag is then placed on a shaker table and agitated under photoradiation until substantially all the fluid has been exposed to the photoradiation. Alternatively, the bag may be prepackaged with powdered photosensitizer and/or powdered additive solution constituents contained therein. The fluid to be decontaminated may then be added through the appropriate port.

Decontamination systems as described above may be designed as stand-alone units or may be easily incorporated into existing apparatuses known to the art for separating or treating blood being withdrawn from or administered to a patient. For example, such blood-handling apparatuses include the COBE Spectra™ or TRIMA® apheresis systems, available from Cobe Laboratories, Inc., Lakewood, Colo., or the apparatuses described in U.S. Pat. No. 5,653,887 and U.S. Ser. No. 08/924,519 filed Sep. 5, 1997 (PCT Publication No. WO 99/11305) of Cobe Laboratories, Inc. as well as the apheresis systems of other manufacturers. The decontamination system may be inserted just downstream of the point where blood is separated and collected just prior to insertion of blood product into a patient, or at any point after separation of blood constituents. The photosensitizer is added to blood components along with the storage or additive solution in a preferred embodiment. It is further contemplated that separate irradiation sources and cuvettes could be placed downstream from collection points for platelets, for plasma and for red blood cells. The use of three separate blood decontamination systems is preferred to placement of a single blood decontamination system upstream of the blood separation vessel of an apheresis system because the lower flow rates in the separate component lines allows greater ease of irradiation. In other embodiments, decontamination systems of this invention may be used to process previously collected and stored blood products.

The endogenous photosensitizers and endogenously-based derivative photosensitizers disclosed herein can be used in pre-existing blood component decontamination systems as well as in the decontamination system disclosed herein. For example, the endogenous photosensitizers and endogenously-based derivative photosensitizers of this invention can be used in the decontamination systems described in U.S. Pat. Nos. 5,290,221 and 5,536,238.

DETAILED DESCRIPTION

Figure 1:
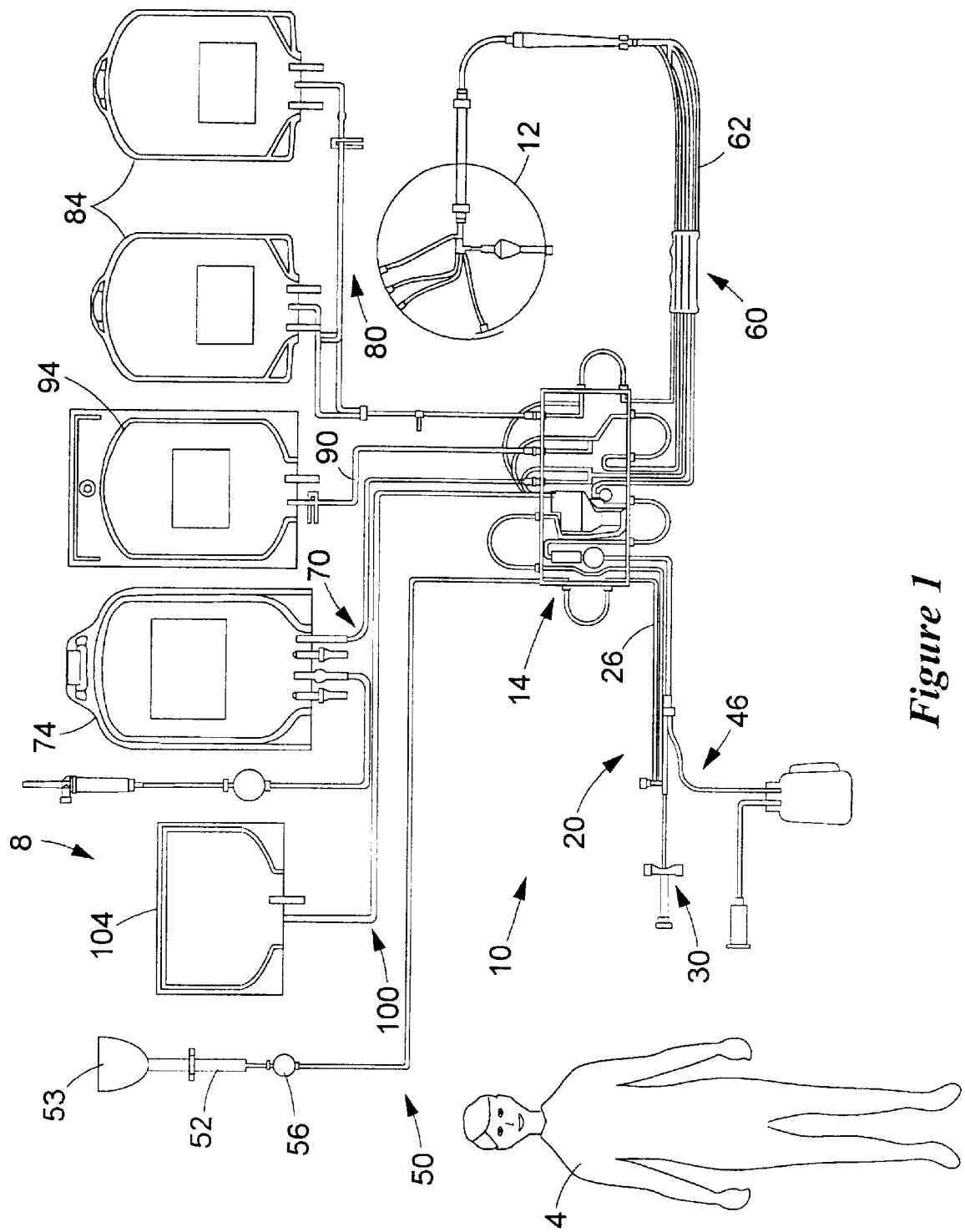
FIG. 1 depicts a blood separation apparatus for collecting a blood component for use with the additive solution of the instant invention.

The decontamination and storage/additive solution of this invention using endogenous photosensitizers and endogenously-based derivative photosensitizers is exemplified herein using 7,8-dimethyl-10-ribityl isoalloxazine as the photosensitizer, however, any photosensitizer may be used which is capable of being activated by photoradiation to cause inactivation of microorganisms. The photosensitizer must be one which does not destroy desired components of the fluid being decontaminated, and also preferably which does not break down as a result of the photoradiation into products which significantly destroy desired components or have significant toxicity.

In accordance with this invention, the fluid to be decontaminated is mixed with photosensitizer and additive storage solution and then irradiated with a sufficient amount of photoradiation to activate the photosensitizer to react with microorganisms in the fluid such that microorganisms in the fluid are inactivated. The amount of photoradiation reaching microorganisms in the fluid is controlled by selecting an appropriate photoradiation source, an appropriate distance of the photoradiation source from the fluid to be decontaminated, an appropriate photopermeable material for the container for the fluid, an appropriate depth to allow full penetration of the photoradiation into the container, and photoradiation enhancers such as one or more additional photoradiation sources, preferably on the opposite side of the container from the first, or reflectors to reflect light from the radiation source back into the container. If a flow through system is used, appropriate flow rates for the fluid in the container and an appropriate container length to allow sufficient time for inactivation of microorganisms present are also selected. Temperature monitors and controllers may also be required to keep the fluid at optimal temperature.

For batch systems, it is preferred to place the fluid to be decontaminated along with the photosensitizer containing additive solutions in bags which are photopermeable or at least sufficiently photopermeable to allow sufficient radiation to reach their contents to activate the photosensitizer. Sufficient photosensitizer along with storage or additive solution is added to each bag to provide inactivation, preferably to provide a photosensitizer concentration of at least about 10 $\mu$M, and the bag is agitated while irradiating, preferably at about 1 to about 200 J/$cm^2$ for a period of between about 6 and about 60 minutes to ensure exposure of substantially all the fluid to radiation. Visible or ultraviolet or a combination of visible light and ultraviolet light may be used. In an alternative embodiment the photosensitizer may be added in dry form as powder, or a pill, tablet or capsule. The fluid to be decontaminated may contain additives or anticoagulant solutions and the blood product or blood components may be stored in such solutions.

The method preferably uses endogenous photosensitizers, including endogenous photosensitizers which function by interfering with nucleic acid replication. 7,8-dimethyl-10-ribityl isoalloxazine is the preferred photosensitizer for use in this invention. The chemistry believed to occur between 7,8-dimethyl-10-ribityl isoalloxazine and nucleic acids does not proceed via singlet oxygen-dependent processes (i.e. Type II mechanism), but rather by direct sensitizer-substrate interactions (Type I mechanisms). Cadet et al. (1983) J. Chem., 23:420–429, clearly demonstrate that the effects of 7,8-dimethyl- 10-ribityl isoalloxazine are due to non-singlet oxygen oxidation of guanosine residues. In addition, adenosine bases appear to be sensitive to the effects of 7,8-dimethyl-10-ribityl isoalloxazine plus UV light. This is important since adenosine residues are relatively insensitive to singlet oxygen-dependent processes. 7,8 dimethyl-10-ribityl isoalloxazine appears not to produce large quantities of singlet oxygen upon exposure to UV light, but rather exerts its effects through direct interactions with substrate (e.g., nucleic acids) through electron transfer reactions with excited state sensitizer species. Since indiscriminate damage to cells and proteins arises primarily from singlet oxygen sources, this mechanistic pathway for the action of 7,8-dimethyl-10-ribityl isoalloxazine allows greater selectivity in its action than is the case with compounds such as psoralens which possess significant Type II chemistry.

FIG. 1 shows a blood apparatus device and apheresis system for collecting blood components for use with the photosensitizer storage solution of this invention. Whole blood is withdrawn from a donor/patient 4 and is provided to an apheresis system or blood component separation device 8 where the blood is separated into the various component types and at least one of these blood component types is removed from the device 8. These blood components may then be provided for subsequent use by another or may undergo a therapeutic treatment and be returned to the donor/patient 4.

In the blood component separation device 8, blood is withdrawn from the donor/patient 4 and directed through an extracorporeal tubing circuit 10 and a blood-processing vessel 12, defining a completely closed and sterile system. The blood component separation device 8 is connected to a pump (not shown). Blood flows from the donor/patient 4 through the extra-corporeal tubing circuit 10 and into rotating blood processing vessel 12. The blood within the blood processing vessel 12 is separated into various blood component types, and these component types (platelets, plasma, red blood cells) are continually removed from the blood processing vessel 12. Blood components which are not being retained for collection or for therapeutic treatment (e.g., red blood cells, white blood cells, plasma if platelets are to be collected) are also removed from the blood processing vessel 12 and returned to the donor/patient 4 via the extracorporeal tubing circuit 10.

Operation of the blood component separation device is preferably controlled by one or more computer processors included therein.

Extracorporeal tubing circuit 10 comprises a cassette assembly 14 and a number of tubing assemblies 20, 50, 60, 70, 80, 90, 100 interconnected therewith. Blood removal/return tubing assembly 20 provides a single needle interface between a donor/patient 4 and cassette assembly 14, and blood inlet/blood component tubing subassembly 60 provides the interface between cassette assembly 14 and blood processing vessel 12. An anticoagulant tubing assembly 50, platelet collection tubing assembly 80, plasma collection tubing assembly 90, red blood cell collection tubing assembly 70 and vent bag tubing subassembly 100 are also interconnected with cassette assembly 14.

The blood removal/return tubing assembly 20 includes a needle subassembly 30 interconnected therewith and anticoagulant tubing 26 connecting to anticoagulant tubing assembly 50 through cassette assembly 14.

Cassette assembly 14 includes front and back molded plastic plates that are hot-welded together to define a rectangular cassette member having integral fluid passageways. The cassette assembly 14 further includes a number of outwardly extending tubing loops interconnecting various integral passageways. The integral passageways are also interconnected to the various tubing assemblies.

Specifically, cassette assembly 14 interconnects with anticoagulant tubing 26 of the blood removal/return tubing assembly 20 and with anticoagulant tubing assembly 50. The anticoagulant tubing assembly 50 includes a spike drip chamber 52 connectable to anticoagulant and photosensitizer source 53 and a sterilizing filter 56. During use, the anticoagulant tubing assembly 50 supplies anticoagulant to the blood removed from donor/patient 4 to reduce or prevent any clotting in the extracorporeal tubing circuit 10. Many anticoagulants are known to the art, e.g. as disclosed in Chapter 3 of the AABB Technical Manual, 11th edition, 1993, including ACD-A, ACD-B, CPD, CP-2D, CPDA-1 and heparin. These as well as cell storage solutions, AS-1, AS-3, AS-5, SAGM, MAP, PAS, PAS II, Plasmalyte A, PAS III, SetaSol, T-Sol, and PSM-1H, are all compatible with the endogenous photosensitizers and endogenously-based derivative photosensitizers described herein.

Cassette assembly 14 also includes an interconnection with blood removal tubing of the blood removal/return tubing assembly 20. Blood passes through pressure sensors, and an inlet filter in cassette assembly 14 and thence to blood inlet tubing 62. Blood inlet tubing 62 is also interconnected with blood processing vessel 12 to provide whole blood thereto for processing.

To return separated blood components to cassette assembly 14, the blood inlet/blood component tubing assembly 60 further includes red blood cell (RBC)/plasma outlet tubing, platelet outlet tubing and plasma outlet tubing interconnected with corresponding outlet ports on blood processing vessel 12. The red blood cell (RBC)/plasma outlet tubing channels the separated red blood cell (RBC)/plasma component through cassette assembly 14 through red blood cell collection tubing assembly 70 to RBC collection bag 74. The platelet outlet tubing channels separated platelets through cassette assembly 14 to platelet collection tubing assembly 80 to platelet collection bags 84. The plasma outlet tubing channels separated plasma through cassette assembly 14 through plasma collection tubing assembly 90 to plasma collection bag 94. Vent bag 104 may be used to vent gases within the system.

Figure 2:
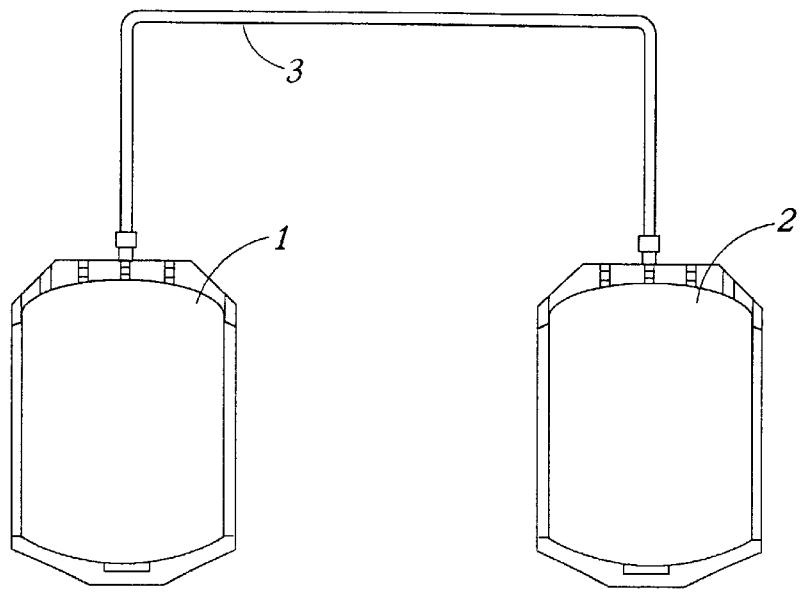
FIG. 2 shows an embodiment of this invention using blood bags which are prepackaged to contain the photosensitizer necessary for inactivation of contaminants in the blood or other bodily fluid.
Figure 3:
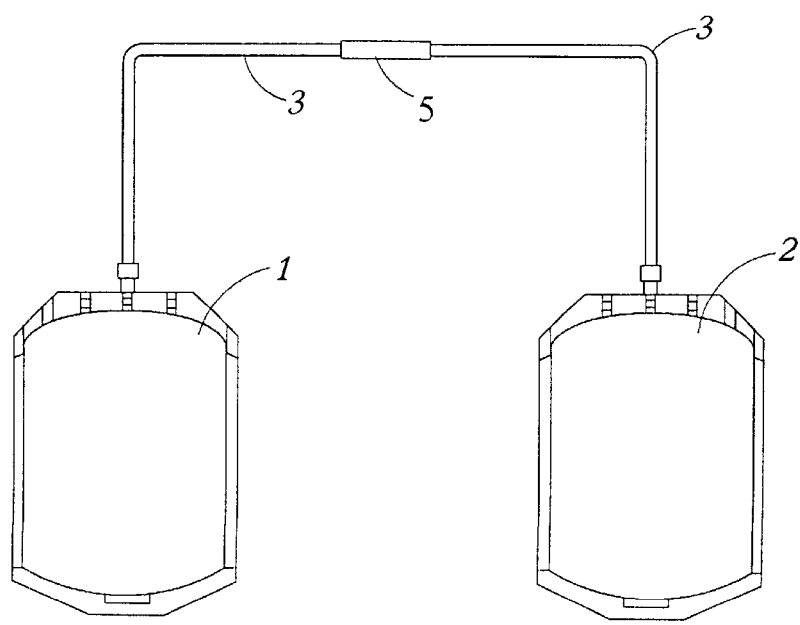
FIG. 3 shows an embodiment of this invention using blood bags as in FIG. 2 with a container in the tubing line between the bags.

FIGS. 2 and 3 depict an embodiment of this invention in which blood bags or other photopermeable containers used in blood storage are prepackaged to contain the photosensitizer in the preferred embodiment of this invention in either dry or aqueous form. The embodiments depicted in these figures may be used with the collected blood component of the system depicted in FIG. 1. The additive constituents necessary for storage of blood components are also pre-packaged either separate from or together with the photosensitizer. It is further understood that the photosensitizer and blood component additives that are prepackaged within the bags may be in a dry powder form, a pill, capsule, tablet form, liquid form, or in various combinations thereof. In describing this invention, the term dry solid or dry form envisions the components being in a loose powdered state or in a solid state such as a pill, capsule, tablet, or any equivalent thereof known to one skilled in the art.

Alternatively, as shown in FIG. 2, a first bag 1 and a second bag 2 are connected together by flexible tubing 3. The first and second bags 1 and 2 could also have a small container 5 located between the two blood bags via flexible tubing 3, as shown in FIG. 3. The container 5 could be another bag, a flask, a reservoir, a small cylinder or any similar container known in the art. The small container 5 of FIG. 3 or the tubing 3 itself of FIG. 2 could contain certain forms of prepackaged components, in a manner similar to that of the two blood bags 1 and 2.

In an alternative embodiment, the photosensitizer, and either blood additive components or physiological saline are prepackaged in a first bag 1. Glucose or another nutrient is the additive component prepackaged with the photosensitizer in bag 1. The blood additive components and photosensitizer may be in a dry solid or in preferably liquid form.

If dry form is used, a solution or preferably saline solution may be added to the bag through a port. A secondary bag 2 is also prepackaged containing preferably bicarbonate and citrate. Upon addition of the separated blood component to the first bag 1 through a port, the resulting media containing blood component, photosensitizer, glucose and additive solution move via the flexible tubing 3 into a second bag 2. The second bag 2 is then disconnected from the first bag 1, mixed, and irradiated. It should be noted however, that either the first bag or the second bag could be irradiated as long as the irradiation is done after the addition of the photosensitizer.

In an alternative embodiment, shown in FIG. 3, the first bag 1 contains prepackaged additive solution either in solid or liquid form. Upon addition of the blood component, the resulting media including the blood component or components, flows through the tubing 3 or small container 5 into the second bag 2. In this embodiment, bicarbonate or another buffer such as phosphate in either a solid or liquid form is located within the tubing 3 or small container 5. When the mixture flows through the tubing 3 or container 5, the bicarbonate or phosphate dissolves upon contact into the mixture. Upon reaching the second bag 2, the media and dissolved bicarbonate or phosphate mixture comes in contact with the prepackaged glucose and photosensitizer in bag 2, either in a solid or liquid form. The second bag 2 is then disconnected from the first bag 1, mixed, and irradiated.

In an alternative embodiment contemplated by this invention, the first bag 1 may contain photosensitizer with or without additive solution, and also with or without glucose and the tubing 3 or small container 5 may contain bicarbonate or phosphate. In another embodiment, the first bag 1 contains additive solution, the photosensitizer is in the tubing 3 or container 5, and bicarbonate or phosphate and/or glucose is in the second bag 2. It is also contemplated that the photosensitizer is prepackaged in the first bag 1, and bicarbonate or phosphate and/or glucose is in the tubing 3 or container 5. The use of a frangible connection (not shown) between the first bag 1 and the container 5 is further envisioned for use with this invention. The frangible connector would be manually snapped to allow fluid or media to reach the constituent in the tubing 3 or container 5 when desired.

In the preferred embodiment, glucose and the photosensitizer are prepackaged in bag 1 to form a first aqueous mixture with bicarbonate and citrate as a second aqueous mixture being prepackaged in bag 2. This packaging configuration is preferred so that the photosensitizer and glucose may be sterilized in a separate bag from the bicarbonate and citrate. Bag 1, containing the photosensitizer and glucose, will typically have a pH range 4–6, while bag 2, containing the citrate and bicarbonate, will have a pH range of 7.0–8.0. Although phosphate can also act as a buffer in this example, bicarbonate is preferred as the buffer as it is more natural to the human body.

Before use and after sterilization the contents of bags 1 and 2 will be mixed in bag 1 to form a third aqueous mixture, for example, (although the contents can also be mixed in the citrate/bicarbonate bag 2). The photosensitizer glucose/citrate/bicarbonate mixture is then combined with the collected blood component, for example, the platelets collected using the apheresis apparatus of FIG. 1. By way of example, the contents of one platelet collection bag 84 may be added to the photosensitizer additive solution mixture in bag 1. The fluid or blood component is then irradiated, as will be further described below. It is also understood that the photosensitizer/additive constituent mixture can be added to bag 84 and the fluid or blood component be irradiated in collection bag 84. The only requirement is that the fluid to be decontaminated or blood component be combined with the photosensitizer and additive constituents after the glucose and photosensitizer have been separately sterilized from the bicarbonate buffer and that the bag used in the irradiation process be permeable to photoradiation.

It is understood that there can be numerous variations of this invention. The additive solutions and other constituents can be prepackaged in either bag in aqueous or in dry solid form as well as within the small container 5. In this system for photoinactivating contaminants within the blood it is also contemplated to add additional bicarbonate or phosphate and a nutrient such as glucose to a known additive bicarbonate or phosphate and glucose free additive solution. It is also desirable to keep the bicarbonate or phosphate separate from the photosensitizer, and also preferable to keep the bicarbonate or phosphate separate from the glucose during bag system sterilization. If the known additive solution contains bicarbonate or phosphate and/or glucose it is contemplated that it may be unnecessary to add an additional amount of such constituents. The above are only a few examples and are not meant to be limiting. It is understood that other combinations of the constituents are also contemplated.

The methods of this invention do not require the use of enhancers such as "quenchers" or oxygen scavengers, however these may be used to enhance the process by reducing the extent of non-specific cell or protein-damaging chemistry or enhancing the rate of pathogen inactivation. Further preferred methods using non-toxic endogenous photosensitizers and endogenously-based derivative photosensitizers do not require removal of photosensitizers from the fluid after photoradiation. Test results show little or no damage to other blood components, e.g. platelets remain biologically active five days post-treatment.

Figure 4:
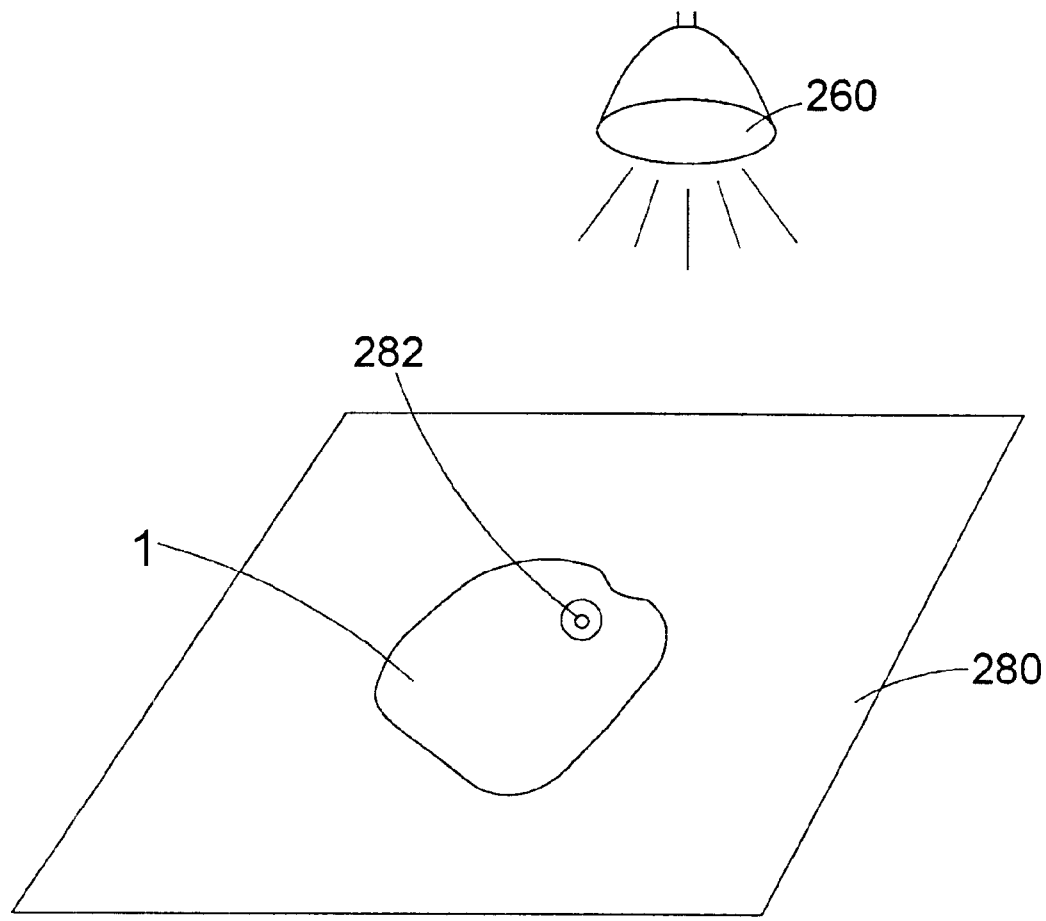
FIG. 4 shows an embodiment of this invention using a blood bag to contain the fluid being treated and photosensitizer and a shaker table to agitate the fluid while exposing to photoradiation from a light source.

FIG. 4 depicts an embodiment of this invention in which the fluid to be decontaminated along with photosensitizer and additive solution, in bag 1, for example, is irradiated. Shaker table 280 is activated to agitate the bag 1 to disperse the photosensitizer/additive solution through the fluid while photoradiation source 260 is activated to irradiate the fluid and photosensitizer in bag 1.

Figure 5:
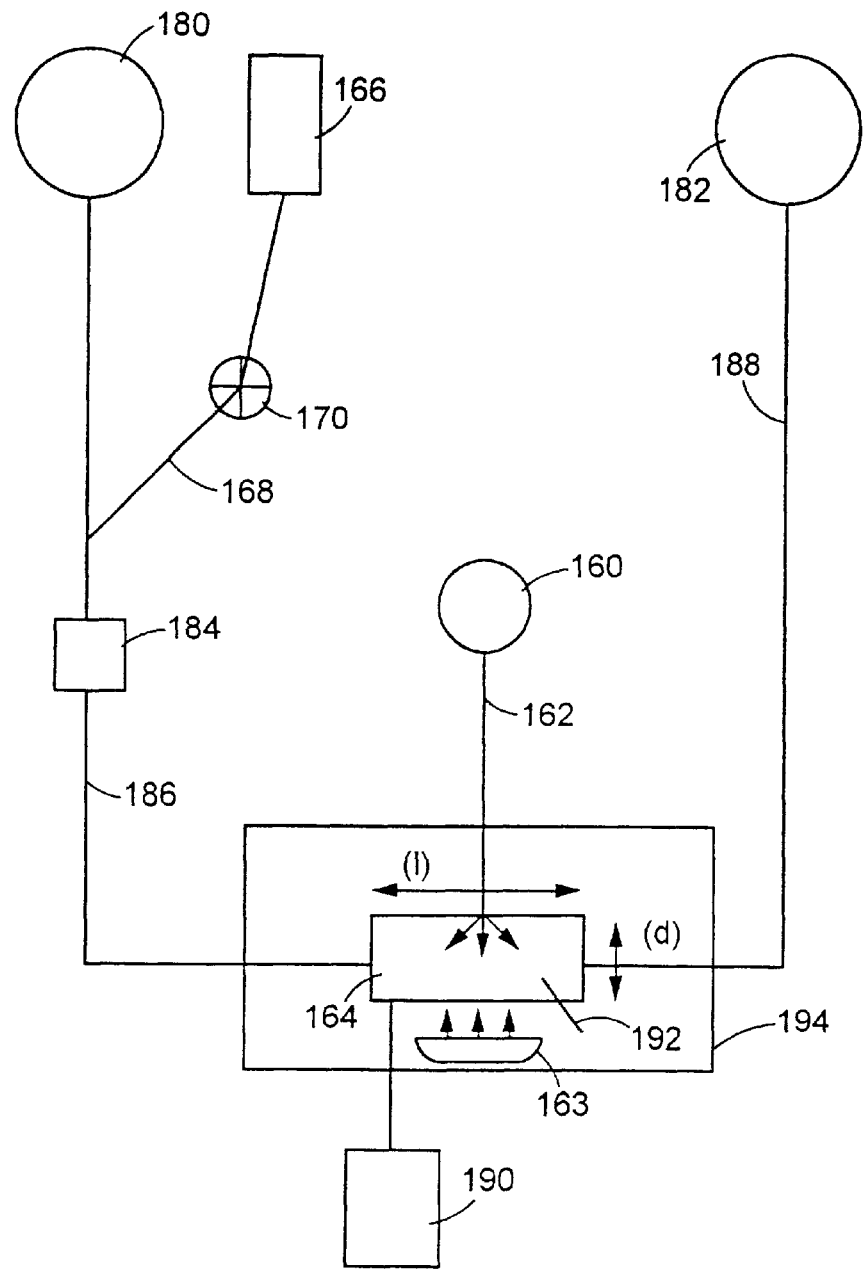
FIG. 5 depicts the decontamination assembly of this invention.

FIG. 5 depicts as an alternative embodiment a stand-alone version of the decontamination assembly of this invention utilizing a flow-through concept. Blood product 180 (which may be recently collected blood or blood component or stored blood, for example, collected platelets in or from bag 84) is connected to blood product line 186 which leads through pump 184 to decontamination cuvette 164. Photosensitizer and additive solution reservoir 166 is connected to photosensitizer input line 168 equipped with input pump 170, and leads into blood product line 186 upstream from decontamination cuvette 164. In the preferred embodiment, the photosensitizer reservoir is filed from the photosensitizer/glucose/bicarbonate/citrate mixture after combining the contents of bags 1 and 2 as described above. Decontamination cuvette 164 is a photopermeable cuvette of a depth (d) and a length (l) selected to ensure decontamination. Cooling system 190 combined with temperature monitor 192 are connected with decontamination cuvette 164 for controlling the temperature of the fluid. Decontamination cuvette 164 is connected via light guide 162 to photoradiation source 160. A photoradiation enhancer 163 is placed adjacent to (either touching or spaced apart from) decontamination cuvette 164 to increase the amount of photoradiation reaching the blood product in the cuvette.

Decontaminated blood product line 188 leads from decontamination cuvette 164 to decontaminated blood product collection 182.

In operation, blood product 180 is conducted into blood product line 186 where it is joined by photosensitizer and additive solution from photosensitizer reservoir 166 flowing at a rate controlled by photosensitizer input pump 170 in photosensitizer input line 168 which joins blood product line 186. The flow rate in blood product line 186 is controlled by pump 184 to a rate selected to ensure decontamination in decontamination cuvette 164. Temperature monitor 192 measures the temperature of fluid in cuvette 164 and controls cooling system 190 which keeps the temperature in the cuvette within a range required for optimal operation. The blood product in decontamination cuvette 164 is irradiated by photoradiation from photoradiation source 160 conducted in light guide 162. The photoradiation source may comprise two or more actual lights. The arrows indicate photoradiation from the end of light guide 162 propagating in the blood product inside transparent decontamination cuvette 164. Adjacent to decontamination cuvette 164 is photoradiation enhancer 163 which may be an additional source of photoradiation or a reflective surface. The arrows from photoradiation enhancer 163 pointing toward decontamination cuvette 164 indicate photoradiation from photoradiation enhancer 163 shining on the blood product material in cuvette 164. Decontaminated blood product exits decontamination cuvette 164 via decontaminated blood product line 188 and is collected at decontaminated blood product collection 182.

In one embodiment using 7,8-dimethyl-10-ribityl isoalloxazine from Sigma Chemical Company as the photosensitizer, a light guide from EFOS Corporation, Williamsville, N.Y. composed of optical fibers is used. The system is capable of delivering a focused light beam with an intensity of 6,200 mW/cm$^2$ in the region of 355–380 nm. It is also possible to use interchangeable filters with the system to achieve outputs of 4,700 mW/cm$^2$ in the spectral region of 400–500 nm. In both cases, the output of light in the region of 320 nm and lower is negligible. Light guides of varying dimensions (3, 5 and 8 mm) are available with this system. The light exits the light guide tip with a 21 degree spread. The 8 mm light guide is appropriate, correctly placed, to adequately illuminate the face of the preferred decontamination cuvette which is a standard cuvette used on Cobe® Spectra disposables sets from Industrial Plastics, Inc., Forest Grove, Oreg.

The flow rate is variable and is determined by the amount of light energy intended to be delivered to the sample. The flow rate is controlled by means of a peristaltic pump from the Cole-Parmer Instrument Company, Vernon Hills, Ill. Flow rates and type of input stream may be controlled via a computer processor as is known to the art.

EXAMPLE

Example 1

Absorbance Profile of 7,8-dimethyl-10-ribityl isoalloxazine

Figure 6:
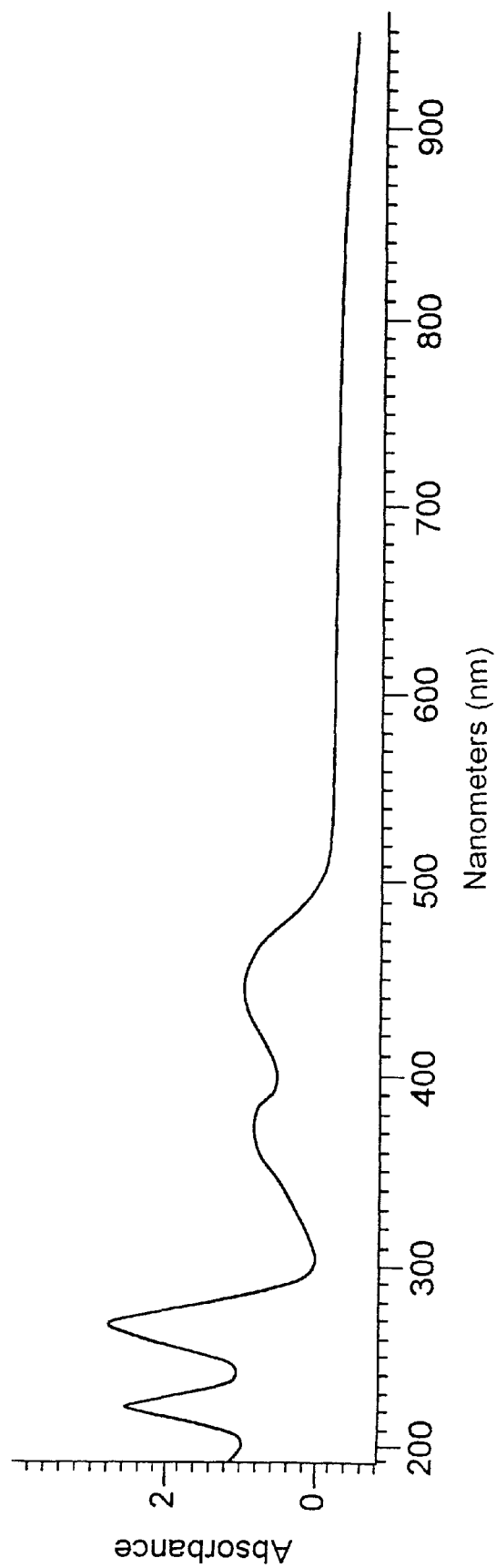
FIG. 6 depicts the riboflavin absorbance spectrum.

A sample of 7,8-dimethyl-10-ribityl isoalloxazine (98% purity) was obtained from Sigma Chemical Company. A portion of this sample was submitted for analysis using a scanning UV spectrophotometer. The range studied covered the region of 200 to 900 nm. For analysis, the sample was dissolved in distilled water. A sample spectrum from this analysis is shown in FIG. 6

Results were consistent with those reported in the literature for the absorbance maxima and extinction coefficients for 7,8-dimethyl-10-ribityl isoalloxazine

| Literature λ max (ε) | Measured λ max (ε) |
|---|---|
| 267 (32,359) | 222 (30,965) |
|  | 265 (33,159) |
| 373 (10,471) | 373 (10,568) |
| 447 (12,303) | 445 (12,466) |

Appropriate wavelengths for irradiation are 373 and 445 nm. The extinction coefficients observed at these absorbance maxima is sufficient to ensure adequate activation of the sensitizer in solution.

Example 2

Solubility of 7,8-dimethyl-10-ribityl isoalloxazine

Solubility in Isolyte S, pH 7.4 Media

The maximum solubility of 7,8-dimethyl-10-ribityl isoalloxazine in Isolyte S media was determined as follows:

7,8-dimethyl-10-ribityl isoalloxazine was mixed with Isolyte S until a precipitate was formed. The mixture was agitated at room temperature for one hour and vortex mixed to ensure complete dissolution of the suspended material. Additional 7,8-dimethyl-10-ribityl isoalloxazine was added until a solid suspension remained despite additional vortex mixing. This suspension was then centrifuged to remove undissolved material. The supernatant from this preparation was removed and analyzed using a spectrophotometer. The absorbance values of the solution were determined at 447 nm and 373 nm. From the extinction coefficients that were determined previously, it was possible to estimate the concentration of the saturated solution Concentration (373)=110 μM=42 μg/mL Concentration (447)=109 μM=40.9 μg/mL Solubility in ACD-A Anticoagulant The same procedure described above was repeated using ACD-A Anticoagulant. The values obtained from these measurements were as follows:

Concentration (373)=166 μM=63 μg/mL

Concentration (447)=160 μM=60.3 μg/mL

The values obtained from these studies indicate an upper limit of solubility of the compound that may be expected.

Example 3

Figure 7:
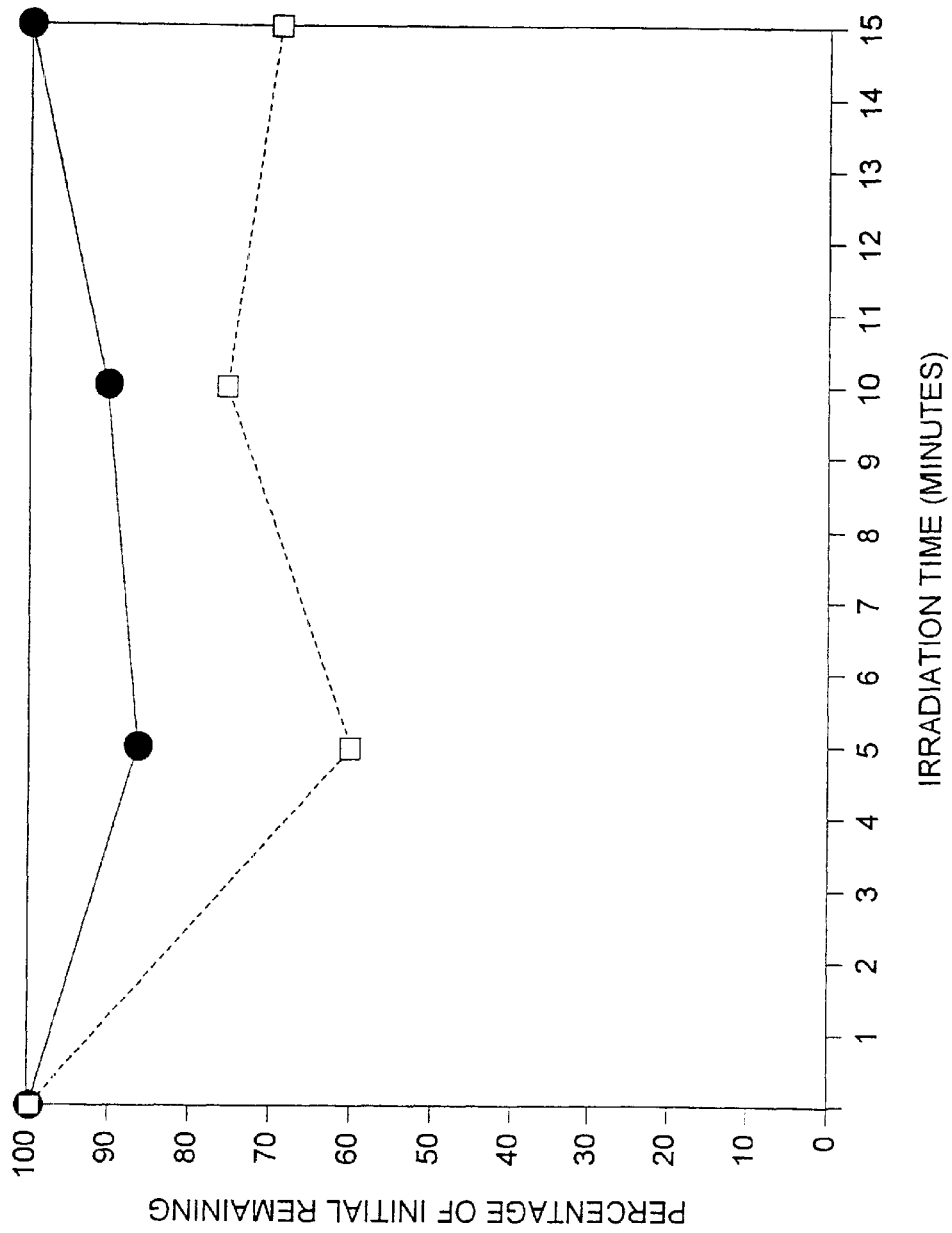
FIG. 7 depicts photodecomposition over time of riboflavin in anticoagulant Acid Citrate Dextrose (ACD) solution. The solid line with circles indicates percent of initial riboflavin remaining at 373 nm. The dotted line with squares indicates percent of initial riboflavin remaining at 447 nm.

Photodecomposition of 7,8-dimethyl-10-ribityl isoalloxazine in Aqueous Media A solution of 7,8-dimethyl-10-ribityl isoalloxazine in Sigma ACD-A was prepared at a concentration of 63 μg/mL. This preparation was taken up into a glass pipette and placed in the path of a UV light source (365 nm max with filters to remove light below 320 nm). The suspension was irradiated for specific intervals at which aliquots were removed for spectroscopic analysis. The absorbance of the dissolved 7,8-dimethyl-10-ribityl isoalloxazine was monitored at 373 and 447 nm at each time interval. The results are depicted in FIG. 7 and Table 1.

TABLE 1

Photodecomposition of 7,8-dimethyl-10-ribityl isoalloxazine
Upon Exposure to UV Light (365 nm) in Acid Solution

| Irradiation Time | % of Initial, 373 nm | % of Initial, 447 nm |
|---|---|---|
| 0 | 100 | 100 |
| 5 | 87.3 | 61.6 |
| 10 | 90.5 | 76.6 |
| 15 | 100 | 70 |

The absorption profile for the solution at 373 nm indicates that no significant decomposition of the reagent occurred over the entire irradiation period. The absorbance of light at this wavelength corresponds to n–π* electronic transitions. The absence of a decrease in the intensity of this peak over time indicates that the ring structure of the molecule is intact despite prolonged irradiation under these conditions.

The absorbance of the molecule at 447 nm is due to π–π* electronic state transitions. The decrease in the absorbance of the molecule at this wavelength with increasing irradiation times is indicative of subtle alterations in the resonance structure of the molecule. This change is most likely due to the loss of ribose from the ring structure of the 7,8-dimethyl isoalloxazine backbone and the formation of 7,8-dimethylalloxozine as a result. These changes are consistent with literature reports on the behavior of the molecule upon irradiation with UV light.

The apparent lack of decomposition of the ring structure of the molecule is in stark contrast to observations with psoralen based compounds under similar conditions. During irradiation, a significant fluorescence of the molecule in solution was observed. This behavior of the molecule is consistent with the resonance features of the ring structure and provides a means for the dissipation of energy in the excited state molecule in a non-destructive fashion.

Example 4

Flow System Concept Evaluation

In order for a flow system to be feasible, the sample must be provided with an adequate flux of light during its presence in the beam path. If the proposed Spectra cuvette were to serve this purpose, then it is possible to estimate the light flux requirements as a function of flow rates through the cuvette as follows:

The volume of solution present in the irradiation zone of the cuvette is ca. 0.375 mls. The transit time for a cell in this region of the cuvette can be determined from the following equation:

$$T = \frac{\text{Volume of Cuvette (mls)}}{\text{Flow Rate (mls/min)}}$$

At 100 mls per minute, the transit time (T) would be 0.00375 min=0.225 seconds.

The energy to which a sample is exposed is dependent on the flux according to the following equation:

$$\text{Energy } (E, \text{Joules/cm}^2) = \frac{\text{Flux } (\phi, \text{mW/cm}^2) * \text{Time } (T, \text{sec.})}{1000}$$

Figure 8:
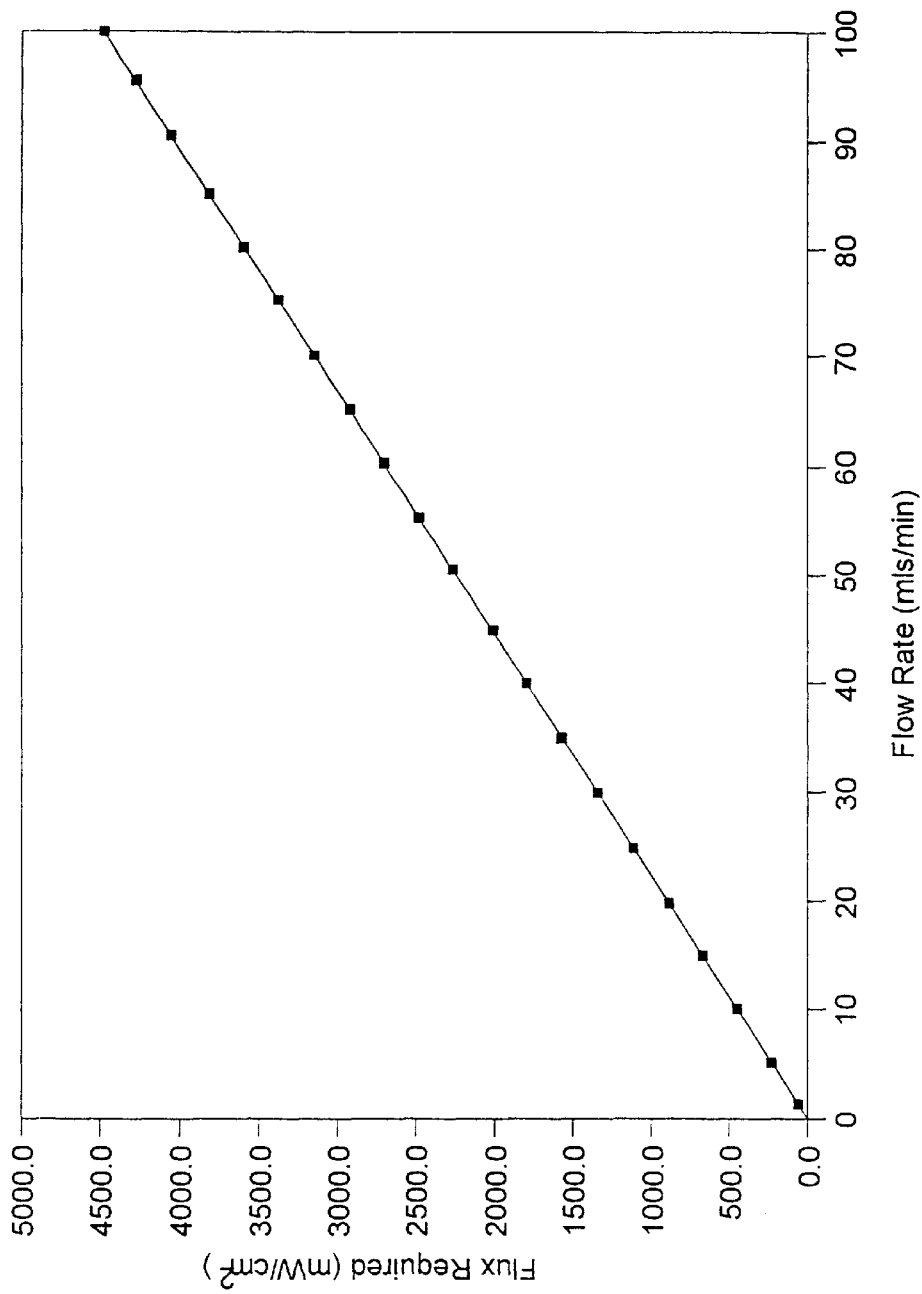
FIG. 8 depicts the light flux required in mW per $cm^2$ as a function of flow rate, i.e. the flux required to deliver one joule/$cm^2$ to a sample in the cuvette.

If we assume that 1 Joule/cm$^2$ is required to activate the sensitizer adequately and the transit time (T) is 0.22 seconds (i.e., flow rate of 100 mls/min through the cuvette), then the required Flux during the sample's transit through the cuvette is 4,545 mW/cm$^2$. A graph depicting the relationship of the required flux from the light source to flow rates through the cuvette is provided in FIG. 8.

These results indicate that, for a flow system to operate properly, UV sources with outputs in the region of Watts/cm$^2$ are required.

Example 5

Effects of Virus Inactivation Treatment on Platelet In Vitro Parameters

Effects of virus inactivation treatment on platelet in vitro parameters were evaluated. Platelet preparations were treated with 7,8-dimethyl-10-ribityl isoalloxazine in combination with UV light. Various in vitro parameters were used as monitors of platelet function in order to determine the extent of changes induced by the treatment conditions. Factors such as energy level of UV light exposure, dose of 7,8-dimethyl-10-ribityl isoalloxazine used, and sample processing conditions were examined for their impact on platelet quality post-treatment. Results from this study are used to establish an appropriate treatment window for inactivation of HIV-1 without compromising platelet function.

Samples were prepared with three different concentrations of 7,8-dimethyl-10-ribityl isoalloxazine. Platelets obtained from a standard Spectra LRS collection were used for these studies.

Starting samples were centrifuged to concentrate the platelet pellet. The pellet was resuspended in a 70:30 (Isolyte S, pH 7.4; McGaw, Inc. Media:Plasma) solution. 7,8-dimethyl-10-ribityl isoalloxazine at the specified concentration, was present in the plasma:media mixture. The platelet suspension was then passed through a UV irradiation chamber at one of three specified flow rates. The flow rates were directly correlated to the energy level of exposure for the cells/media mixture which passes through the irradiation chamber. After flowing through the irradiation chamber, samples were stored in a citrate plasticized sampler bag for subsequent analysis.

Following irradiation, in vitro measurements of platelet function, including hypotonic shock response (HSR), GMP-140 expression, pH, pCO$_2$, pO$_2$, platelet swirl, and cell count, were evaluated in order to determine the effects of the treatment protocol on cell quality.

Platelet quality was monitored as a function of irradiation conditions (sensitizer concentration and flow rates/Energy levels). The platelet quality includes parameters such as HSR response, GMP-140 activation, etc. The flow rates that are studied can be related to the Energy of exposure as follows:

$$\text{Transit Time } (T, \text{sec}) = \text{Exposure Time} = \frac{0.375 \text{ mls}}{(F_r/60)}$$

$F_r$ = Flow Rate (mls/min)

0.375 mls = Cuvette Volume (mls)

$$\therefore T \text{ (sec)} = \frac{22}{F_r}$$

$$\text{Energy (Joules/cm}^2) = \frac{\text{Flux } (\phi, \text{mW/cm}^2) * T \text{ (sec)}}{1000}$$

$$E = \frac{\phi * 0.022}{F_r}$$

The effect of energy of UV exposure and concentration of 7,8-dimethyl-10-ribityl isoalloxazine on the stability and viability of treated platelets was evaluated. Three energy levels and three concentration levels were evaluated as follows:

| Energy Levels: | 1,5,9 J/cm$^{2*}$ |
|---|---|
| 7,8-dimethyl-10-ribityl isoalloxazine Concentrations: | 1, 50, 100 μM** |

*Levels of total energy exposure were determined by the flow rate of the suspension through the irradiation chamber in accordance with the conversion chart of Table 2
**Since the media is diluted 70:30 (Media:Plasma) the stock concentration of 7,8-dimethyl-10-ribityl isoalloxazine in media alone prior to mixing with the plasma was adjusted appropriately.

This required starting concentrations in Isolyte S of 1.43, 71.4, and 143 μM.

TABLE 2

Energy Exposure Levels as a Function of Flow Rate Through the Irradiation Chamber

| Energy Delivered (J/cm$^2$) | Flow Rate (mls/min) | Time to process 20 mls minutes |
|---|---|---|
| 1 | 16.90 | 1.18 |
| 2 | 8.45 | 2.37 |
| 3 | 5.83 | 3.55 |
| 4 | 4.22 | 4.73 |
| 5 | 3.38 | 5.92 |
| 6 | 2.82 | 7.10 |
| 7 | 2.41 | 8.29 |
| 8 | 2.11 | 9.47 |
| 9 | 1.88 | 10.65 |
| 10 | 1.69 | 11.84 |

Flux=3640 mW/cm$^2$; chamber volume=0.117 mls.
Values for treated samples were compared to control groups. The control samples included the following:

Untreated Sample in Plasma (Historical Control)
+Flow-UV-7,8-dimethyl-10-ribityl isoaloxazine
Procedure A normal donor platelet apheresis product was obtained from an AABB accredited blood banking facility. The sample was collected using standard Spectra LRS® procedures. All manipulations or procedures described below were performed with standard laboratory safety procedures and methods. The unit number and blood type were recorded. All samples were used within 24 hours of collection. Aseptic procedure was followed for all sample transfers and processing steps.

The sample was transferred to a 500 mls PVC transfer pack and centrifuged at 5000×g for five minutes to pack the platelets. Plasma was then removed from the platelet pellet using a standard plasma press. The plasma was retained for further use. The plasma removed from the cell pellet was then mixed with a stock solution of Isolyte S, pH 7.4; McGaw, Inc. This stock solution of media was prepared by adding a pre-determined amount of 7,8-dimethyl-10-ribityl isoalloxazine to Isolyte S to provide final concentrations of 1.43, 71.4, and 143 μM. Following addition of 7,8-dimethyl-10-ribityl isoalloxazine the stock solution was filtered through a 0.22 μM sterile filter. The stock solution was then mixed with autologous plasma in a 70:30 (v:v) ratio to provide final 7,8-dimethyl-10-ribityl isoalloxazine concentrations of 1, 50, and 100 μM respectively. During preparation of the 7,8-dimethyl-10-ribityl isoalloxazine stock solutions, care was taken to avoid exposure to light. Samples were prepared according as follows:

| 1 μM | 2 samples |
|---|---|
| 100 μM | 2 samples |
| 50 μM | 1 sample |

The platelet pellet was then resuspended in the plasma-:media mixture to the original volume of the starting sample. The sample was connected to a flow apparatus comprising a container for cells and photosensitizer, a container for media, said containers being connected via valved lines to a single line for mixed cells/sensitizer and media equipped with a pump. Mixed cells/sensitizer and media were flowed into a cuvette held in a holder with a mirrored wall, irradiated by a light source. This irradiation chamber was equipped with a temperature probe. After passing through the cuvette, fluid was collected in a product bag.

The tubing set was initially primed with Isolyte S media. Five minutes prior to the start of the test sample flow, the light source was activated. Temperature was monitored during this interval and kept lower than 32° C. in the irradiation chamber.

The flow rate for the sample through the irradiation chamber was determined by the chart of Table 2. Flow rates which provide total irradiation energy levels of 1, 5 and 9 J/cm$^2$ were utilized according to the following testing matrix:

Sample Run #1: 7,8-dimethyl-10-ribityl isoalloxazine Concentration=1 μM
  A. +7,8-dimethyl-10-ribityl isoalloxazine+1 J/cm$^2$
  B. +7,8-dimethyl-10-ribityl isoalloxazine+9 J/cm$^2$
Sample Run #2: 7,8-dimethyl-10-ribityl isoalloxazine=100 μM
  A. +7,8-dimethyl-10-ribityl isoalloxazine+1 J/cm$^2$
  B. +7,8-dimethyl-10-ribityl isoalloxazine+9 J/cm$^2$
Sample Run #3: 7,8-dimethyl-10-ribityl isoalloxazine=50 μM
  A. +7,8-dimethyl-10-ribityl isoalloxazine+5 J/cm$^2$
Sample Run #4: Control Sample, 7,8-dimethyl-10-ribityl isoalloxazine=0 μM
  A. +Flow-UV-7,8-dimethyl-10-ribityl isoalloxazine All samples were identified by the run number and sample letter designation corresponding to treatment condition (i.e., 1A). Each sample set was run for a total of 2 replicates. The order in which samples were treated was determined by assignment according to a random number generator.

A sample volume of 20 mls per run condition was collected for each sample. These samples were collected into citrate plasticized sampling bags (53 mls total volume) and stored for analysis. The temperature of the sample and the irradiation chamber was noted at the start, mid-point, and end of each run.

An initial aliquot from each preparation was removed post-treatment for analysis. Parameters for analysis included cell count, pH, pCO$_2$, pO$_2$, platelet swirl, HSR, and GMP-140 analysis. The remaining portion of the sample was placed in an end-over-end platelet agitator in a +22 incubator and stored for five days post-treatment. On day 5, a second aliquot was removed and analyzed for the same in vitro parameters.

The following equipment was used: Nikon Labophot microscope; Serono-Baker System 9000 Hematology Analyzer; analytical balance; platelet incubator (+22 Celsius) and rotator; laboratory refrigerator (+4 Celsius); Mistral 3000i Centrifuge; Corning Blood Gas Analyzer; Becton-Dickinson FACSCALIBUR Flow Cytometer; UV irradiation chamber; UV radiometer (UVX Radiometer, UVP, Inc.); EFOS Ultracure 100SS Plus (365 nm maximum output and 340 nm bandpass filters); and temperature probe (thermocouple).

Results for each set of test variables were compared for the defined conditions of energy of exposure and concentration of 7,8-dimethyl-10-ribityl isoalloxazine. Direct comparison to the untreated control sample was made and significant differences defined by a probability p>0.05 from a paired, one-tailed, Student's T-Test analysis.

The results from these studies were summarized as follows:

1. At sensitizer concentrations in excess of 10 $\mu$M and platelet concentrations above 1.5E+06/$\mu$L, there was a drop in sample pH by day 2. The pH declined steadily beyond day 2 of storage reaching unacceptable levels (<6.5) by day 3 of storage. All other in vitro parameters followed the pattern observed with sample pH.
2. This decrease in sample pH occurred regardless of whether or not the sample was exposed to UV light.
3. At platelet concentrations of 5.4E+05/$\mu$L, there was no drop in sample pH after extended storage at any sensitizer concentration studied up to 100 $\mu$M.
4. At sensitizer concentrations up to 10 $\mu$M, platelet concentrations above 1.5E+06/$\mu$L, and UVA levels up to 10 J/cm2, measured platelet properties were comparable to control, untreated cells. These remained comparable to control levels after five or more days of storage post-treatment.

These studies on platelet function post-treatment provided a clear window in which cell properties were maintained at levels comparable to untreated cells. The results also indicated that by varying the storage or treatment conditions for the cells this window can be expanded. The observed effect of 7,8-dimethyl-10-ribityl isoalloxazine with or without UV light on sample pH suggests a metabolic effect of this additive which may be moderated by changes in the storage or processing conditions of the samples.

Example 6

A platelet concentrate was mixed with the platelet additive solution Isolyte S at a ratio of 20:80 platelet concentrate:Isolyte S. Mixtures of platelet concentrates and platelet additive solutions are referred to herein as in "media." Platelet concentrate without additive solution is referred to herein as in "plasma." Both were spiked with *Listeria monocytogenes*. Vitamin K5 was then added to each in the amount of 300 $\mu$g/mL B. Each was then exposed to UV, visible or room light in the cuvette apparatus of FIG. 5 with the results shown in Table 3.

TABLE 3

| | Log Inactivation (cfu/mL) | |
| --- | --- | --- |
| | K5 in Media | K5 in Plasma |
| UV, 40 J/cm² | 4.2 Logs | 0.1 Logs |
| VIS, 40 J/cm² | 4.2 Logs | 0.1 Logs |
| Room Light | 0 Logs | 0 Logs |

UV Light = 365 nm
VIS Light = 419 nm
Pathogen = *Listeria monocytogenes*
Concentration of K5 = 300 $\mu$g/mL Example 7

Figure 9:
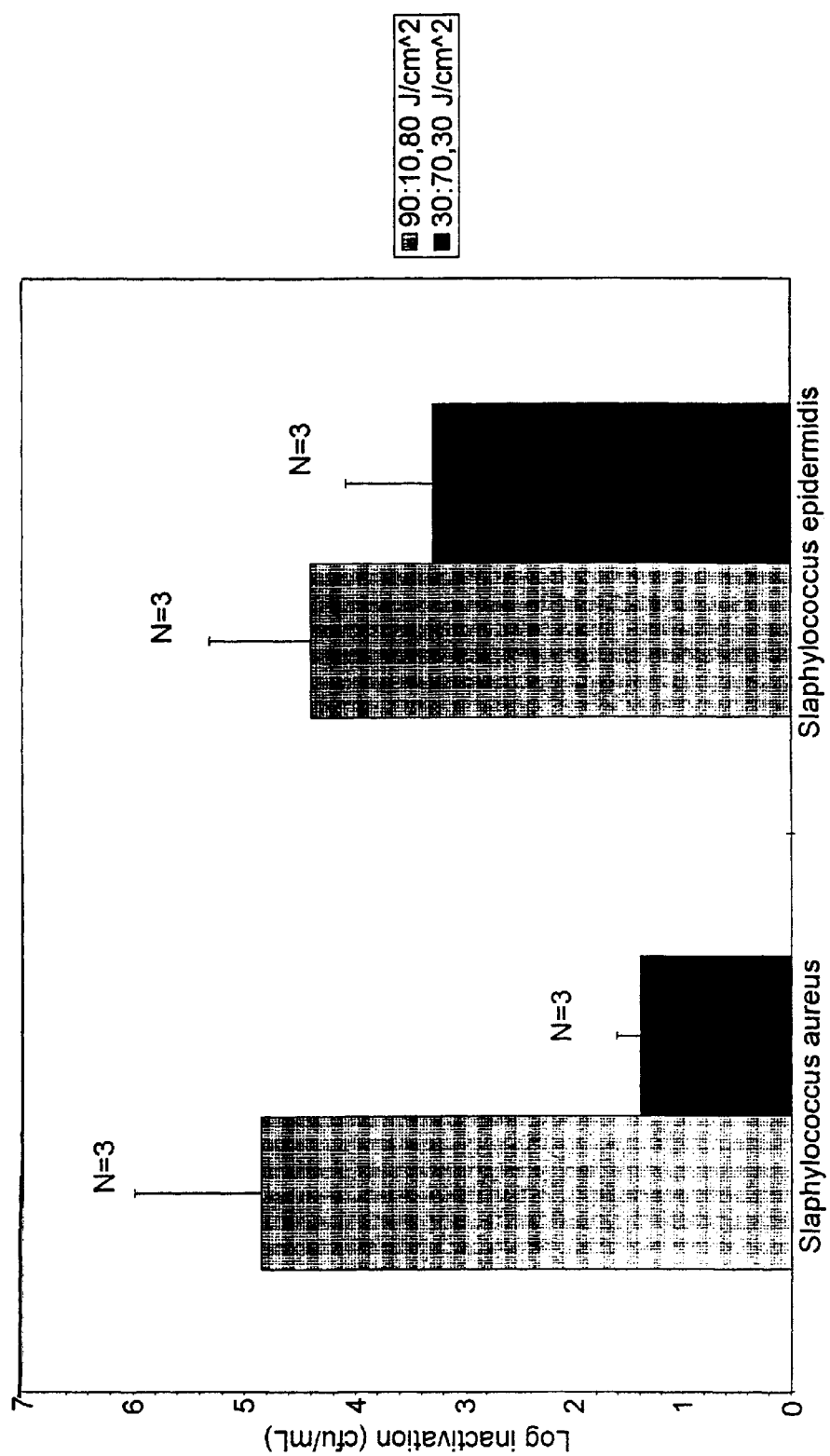
FIG. 9 depicts inactivation of bacteria as a function of platelet preparation and energy of irradiation, using 90% platelets and 10% platelet additive solution (90:10) and 30% platelets with 70% additive solution (30:70).

To platelet concentrate as described in Example 6 and to 70:30 media as described in Example 10 was added 10 $\mu$M of 7,8-dimethyl-10-ribityl isoalloxazine. The platelet concentrate and media were spiked with *S. aureus* or *S. epidermidis*, and irradiated at 80 J/cm² and 30 J/cm² and inactivation measured as above. Results are shown in FIG. 9.

Example 8

To platelet concentrate as described in Example 6 was added 7,8-dimethyl-10-ribityl isoalloxazine, alloxazine mononucleotide, or 7-8-dimethyl alloxazine, followed by spiking with *S. aureus* or *S. epidermidis*, and irradiation at 80 J/cm². Inactivation results are shown in Table 4.

TABLE 4

| | Log Inactivation (cfu/mL) | |
| --- | --- | --- |
| | *Staphylococcus aureus* | *Staphylococcus epidermidis* |
| 7,8-dimethyl-10-ribityl isoalloxazine, 10 $\mu$M | 1.9 Logs | 4.1 Logs |
| alloxazine mononucleotide, 10 $\mu$M | 1.6 Logs | 5.6 Logs |
| 7-8-dimethyl alloxazine, 7 $\mu$M | 1.6 Logs | 2.9 Logs |

Example 9

Figure 10:
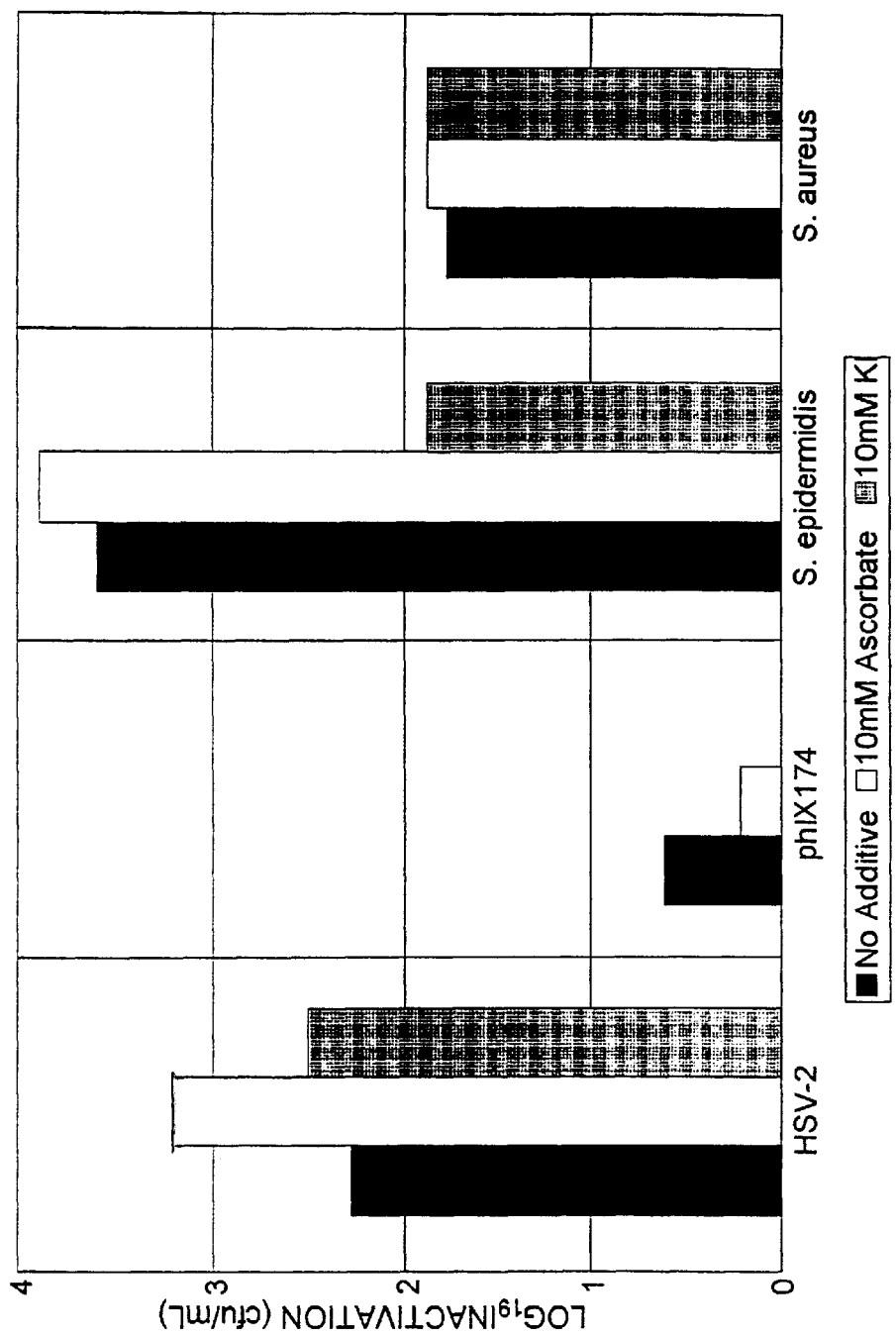
FIG. 10 shows the effect on inactivation of virus, bacteriophage and bacteria of adding antioxidants to platelet concentrate.

To platelet concentrate of Example 6 was added 10 M 7,8-dimethyl-10-ribityl-isoalloxazine. Aliquots contained no additive, 10 mM ascorbate or 10 mM KI as a "quencher" or antioxidant. The solutions were spiked with HSV-2, X174, *S. epidermidis* or *S. aureus* and irradiated at 80 J/cm². Results are shown in FIG. 10.

Example 10

Figure 11:
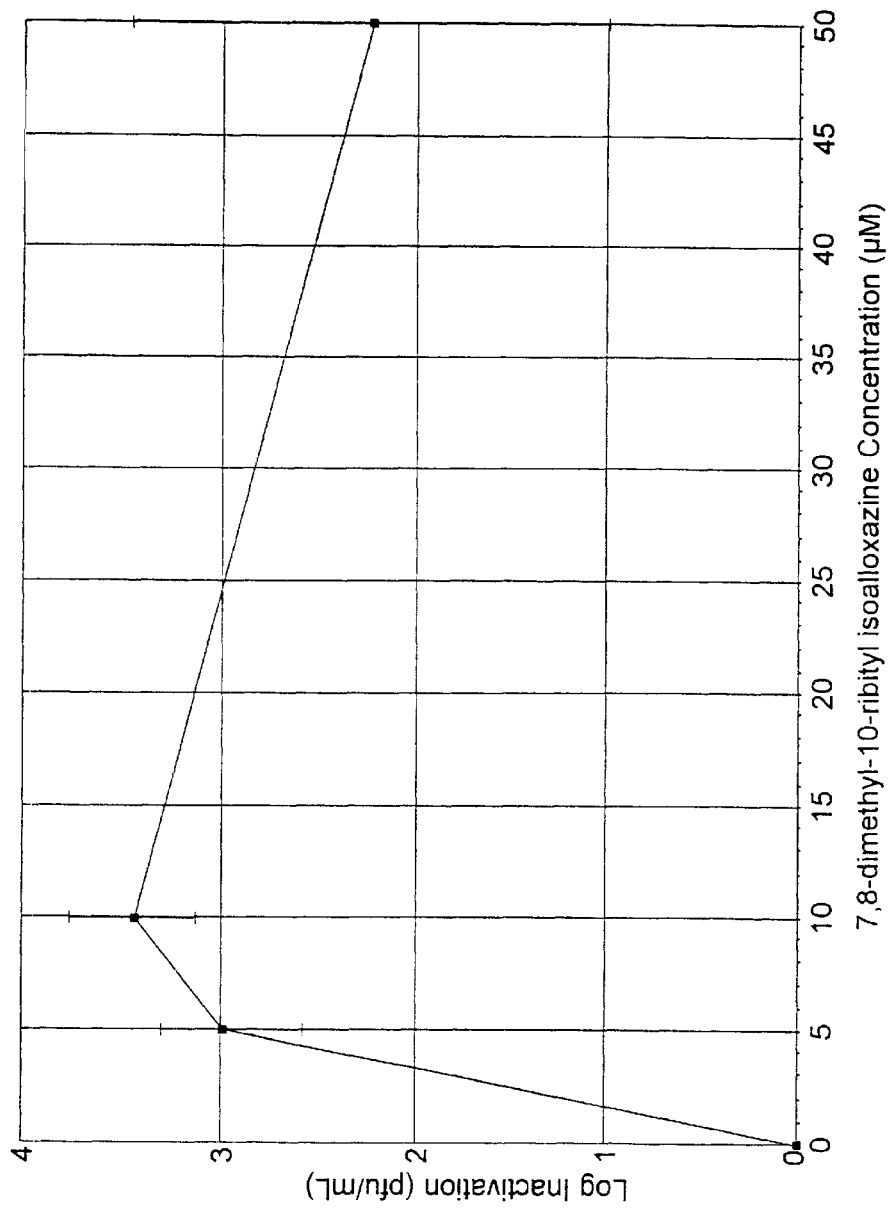
FIG. 11 shows the inactivation curve for Herpes Simplex type II virus as a function of concentration of photosensitizer at an energy of irradiation of 20 J/$cm^2$ using half ultraviolet and half visible light.

To platelet concentrates of Example 6 were added varying concentrations of 7,8 dimethyl-10-ribityl-isoalloxazine. These solutions were spiked with herpes simplex virus type II (HSV-II), a double-stranded DNA envelope virus. Irradiation was done at 80 J/cm². The experiment was replicated three times. In all three trials complete inactivation was achieved. Results are shown in FIG. 11.

Example 11

Figure 12:
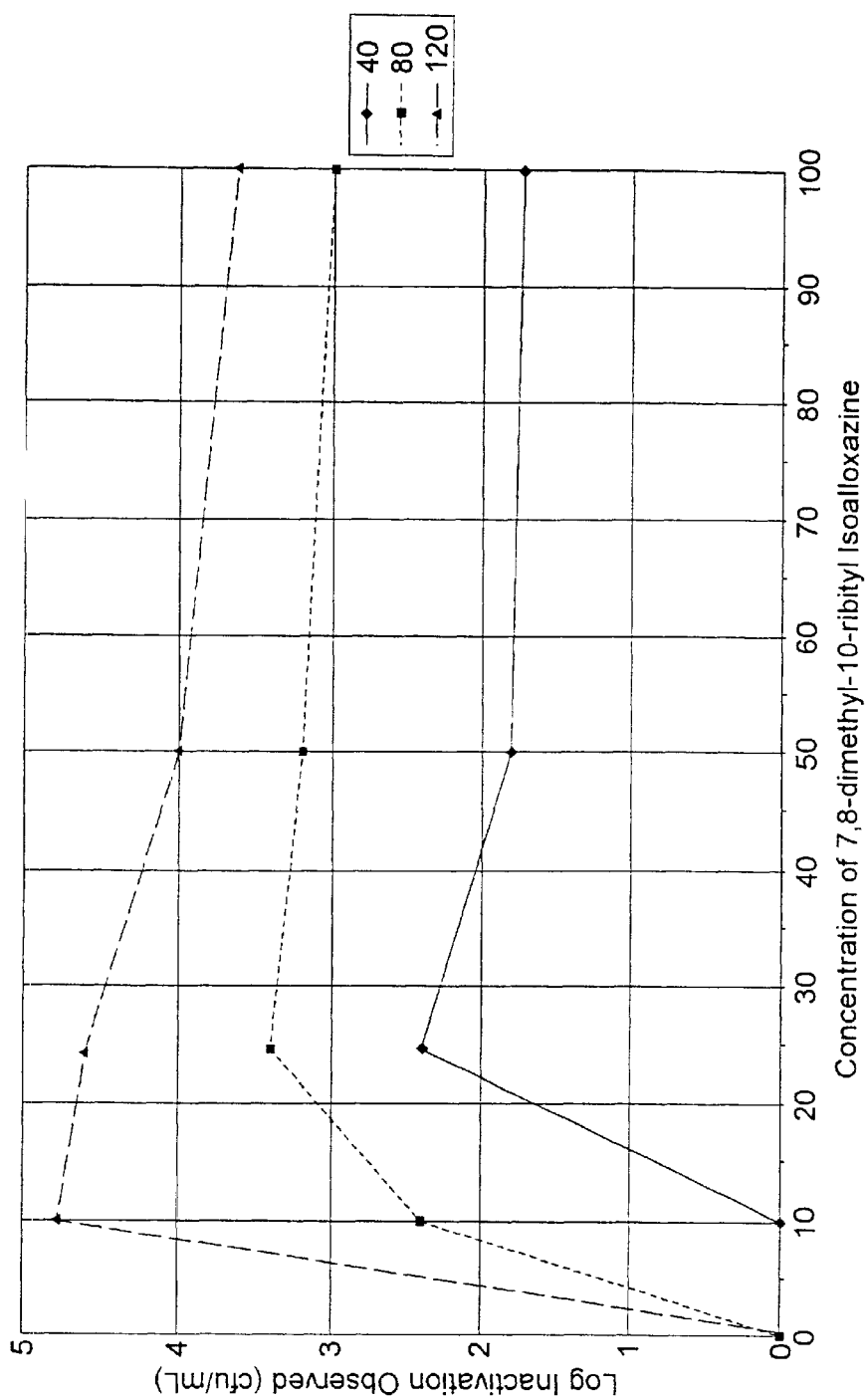
FIG. 12 shows inactivation of S. epidermidis at varying concentrations of photosensitizer and energies of irradiation.

The protocol of Example 10 was followed using *S. epidermidis* instead of HSV II at energies of irradiation of 40, 80 and 120 J/cm². Inactivation results are shown in FIG. 12.

Example 12

Figure 13:
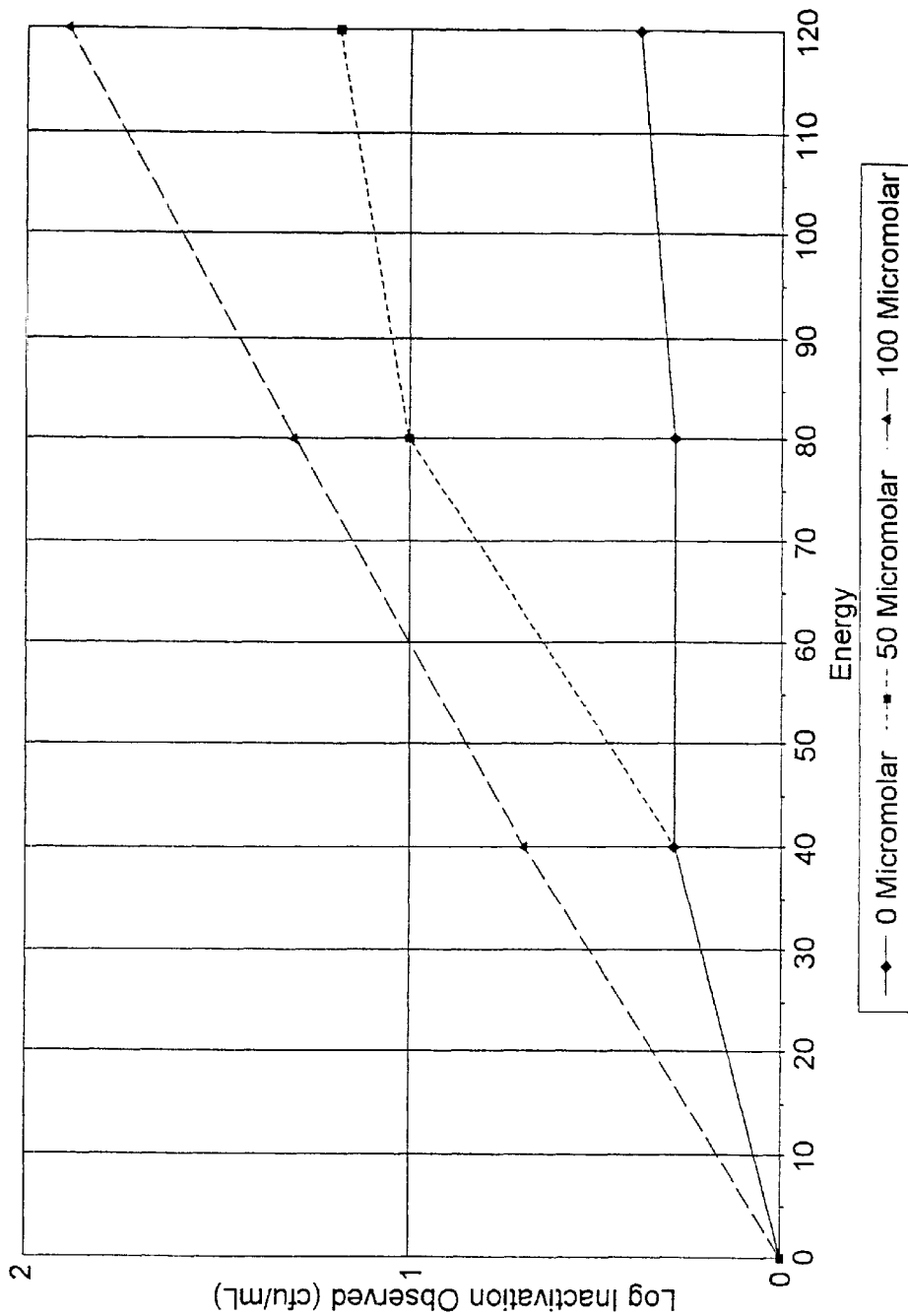
FIG. 13 shows inactivation of ΦX174 at varying concentrations of photosensitizer and energies of irradiation.

The protocol of Example 10 was followed using X174, a single stranded DNA bacteriophage, at varying concentrations of 7,8-dimethyl-10-ribityl-isoalloxazine and energies of irradiation. Inactivation results are shown in FIG. 13.

Example 13

Figure 14:
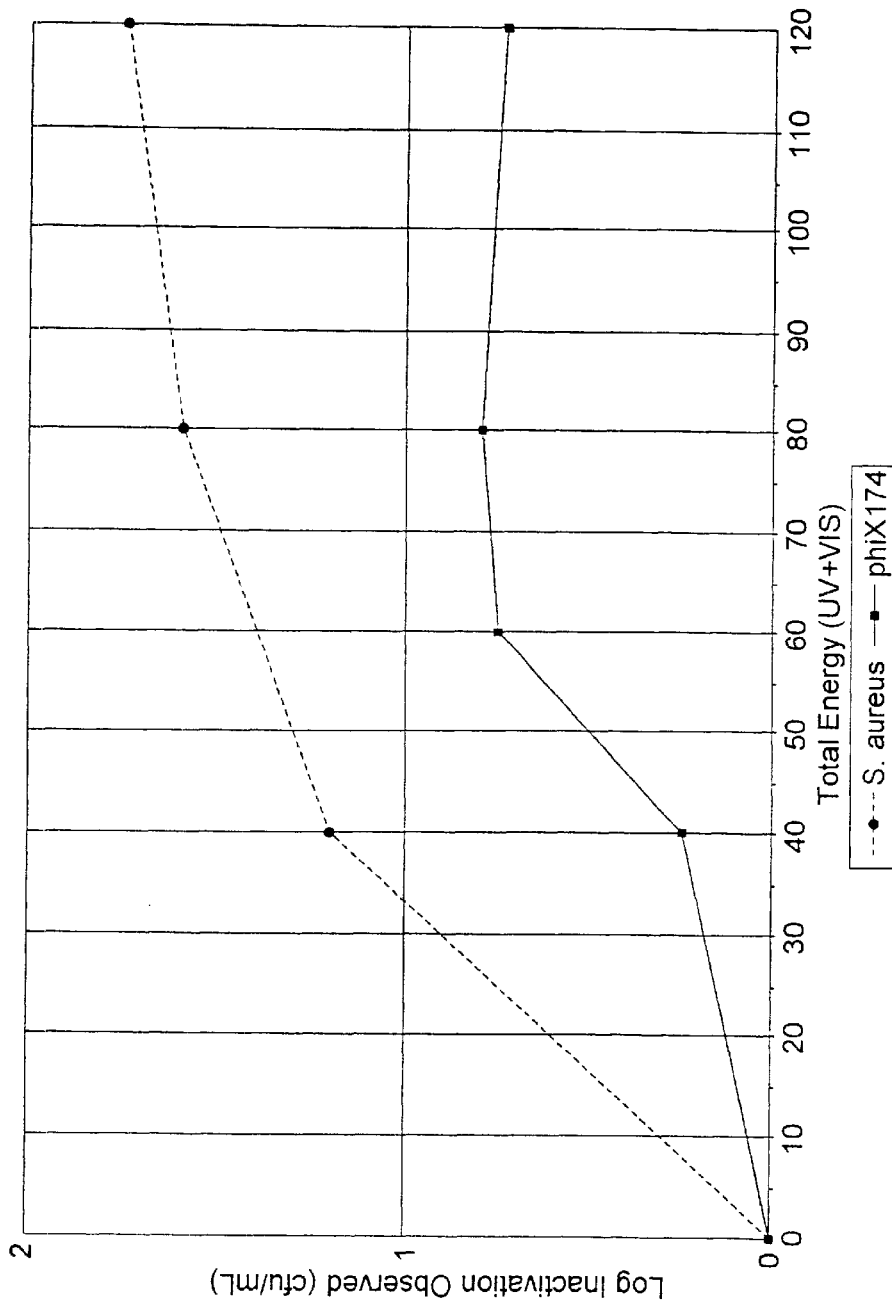
FIG. 14 shows inactivation of S. aureus and ΦX174 at varying energies of irradiation using a 50:50 mixture of ultraviolet and visible light.

To platelet concentrates of Example 6 was added 10 M 7,8-dimethyl-10-ribityl-isoalloxazine. These were spiked with *S. aureus* or X174 and irradiated at varying energies of irradiation with a 50:50 mixture of visible and ultraviolet light. Inactivation results are shown in FIG. 14.

Example 14

Figure 15:
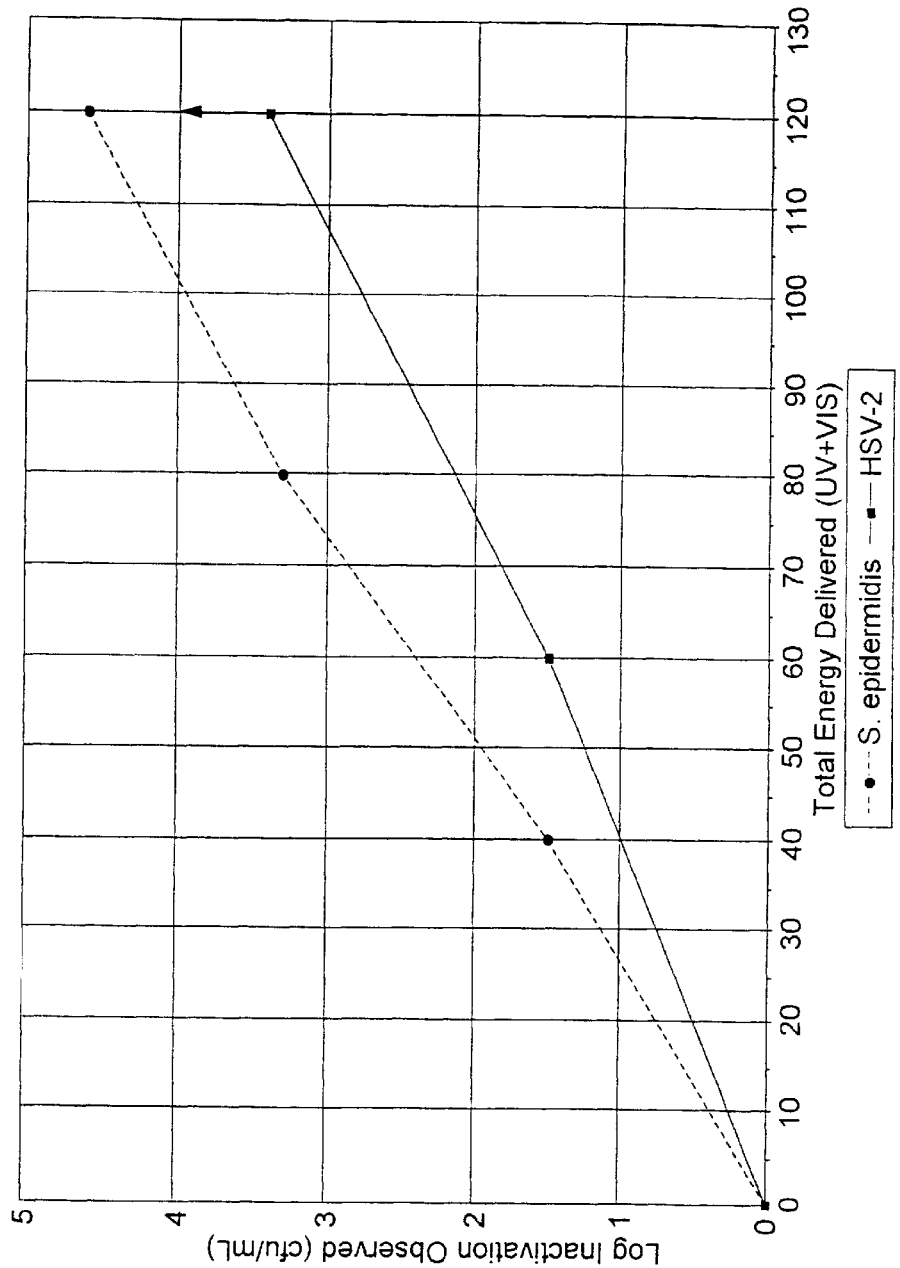
FIG. 15 shows inactivation of S. epidermidis and HSV-II at varying energies of irradiation using a 50:50 mixture of ultraviolet and visible light.

The protocol of Example 13 was followed using *S. epidermidis* and HSV-II as the microorganisms. A 50:50 mixture of ultraviolet and visible light was supplied by DYMAX light source. Inactivation results are shown in FIG. 15.

Example 15

Figure 16:
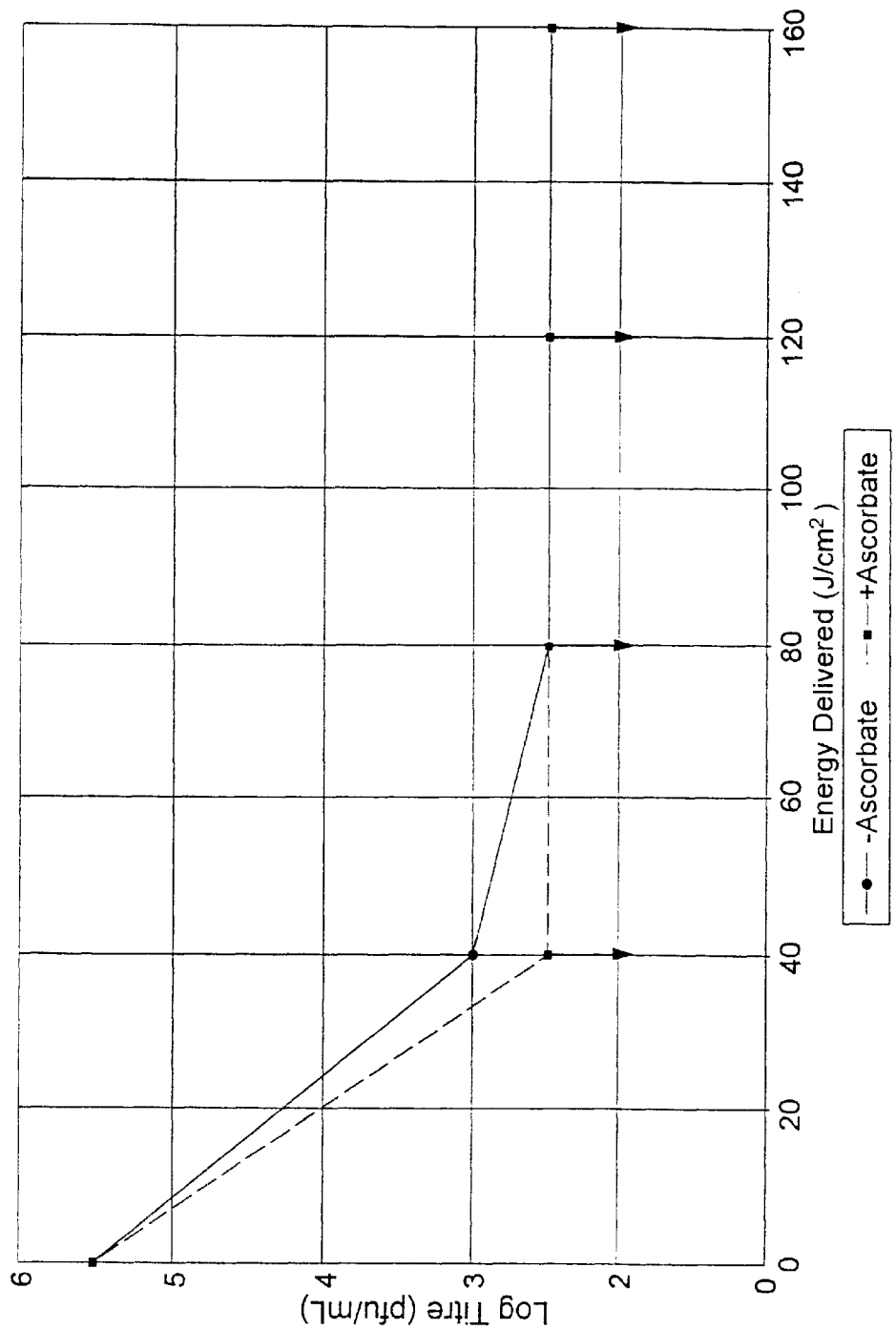
FIG. 16 shows inactivation of HSV2 virus in blood bags agitated and irradiated at varying energy levels.

To platelet concentrate of Example 6 was added 10 M 7,8-dimethyl-10-ribityl-isoalloxazine in powdered form. Tests with and without added ascorbate were conducted. 150 ml of the test solutions were placed in a Spectra™ blood bag and shaken and exposed to varying energies of irradiation using 50:50 visible:ultraviolet light. After receiving 40 J/cm$^2$, the contents of each bag were transferred to a new bag to avoid errors due to microorganisms which may have remained in the spike port of the bag. Inactivation results are shown in FIG. 16. Downward arrows indicate inactivation to the level it was possible to detect (2.5 log titre).

Example 16

Figure 17:
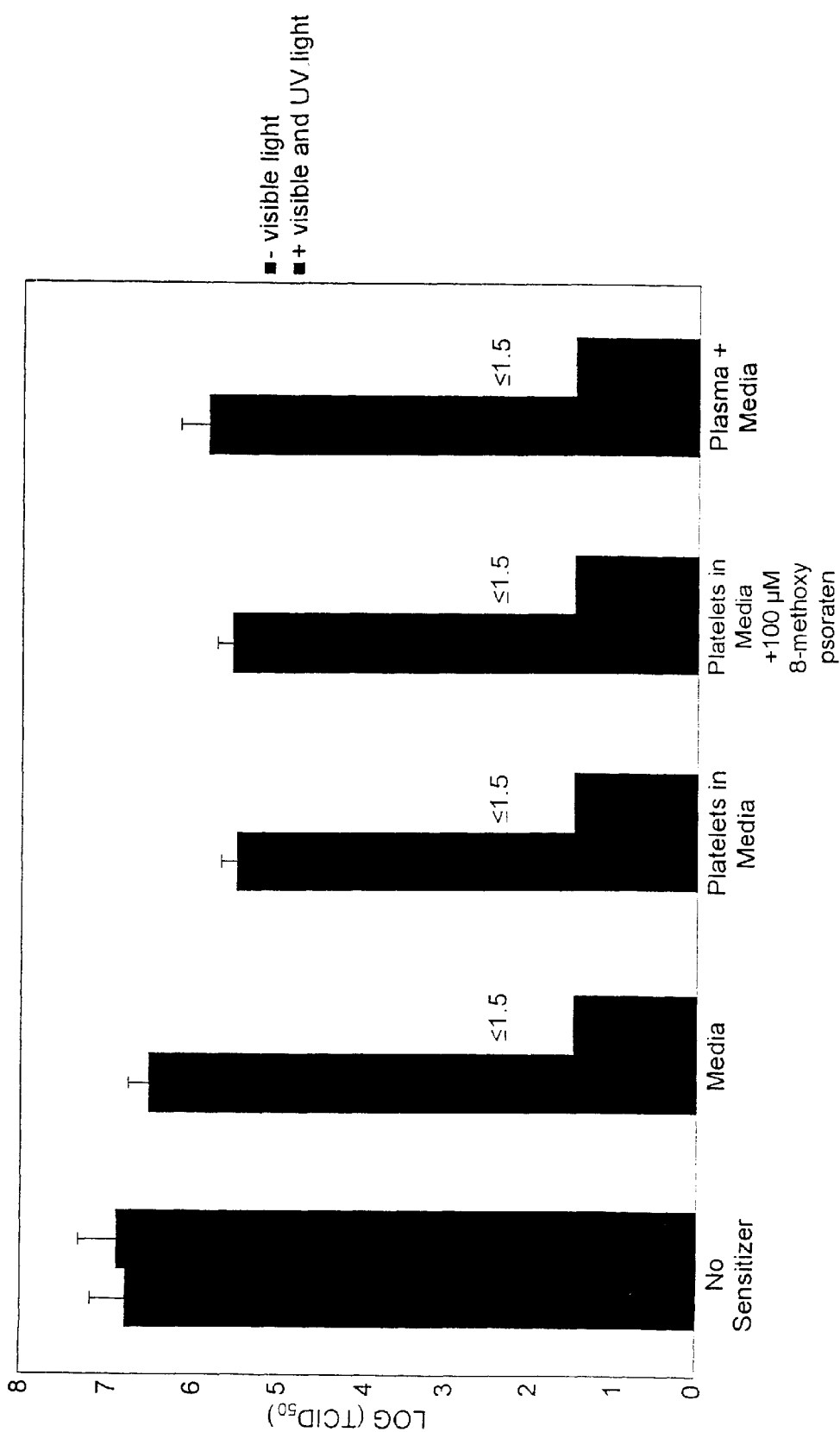
FIG. 17 compares inactivation results for vaccinia virus in various fluids using ultraviolet light alone or 50:50 visible and ultraviolet light.

To platelet concentrate of Example 6 and platelet concentrate in Isolyte S at 30:70 platelet concentrate:Isolyte S, was added 20 M 7,8-dimethyl-10-ribityl-isoalloxazine. These were spiked with vaccinia virus, a double stranded DNA envelope virus, and exposed to 60 J/cm$^2$ visible light or mixed (50:50) visible and ultraviolet light using a DYMAX 2000 UV light source for 30 minutes. The limit of detection was 1.5 logs. Inactivation results are show in FIG. 17. Comparisons were done using no photosensitizer, photosensitizer in Isolyte S media alone, platelets in Isolyte S media, platelets in Isolyte S media using 8-methoxy psoralen instead of 7,8 dimethyl-10-ribityl-isoalloxazine, and platelet concentrate in Isolyte media (30:70).

Example 17

Figure 18:
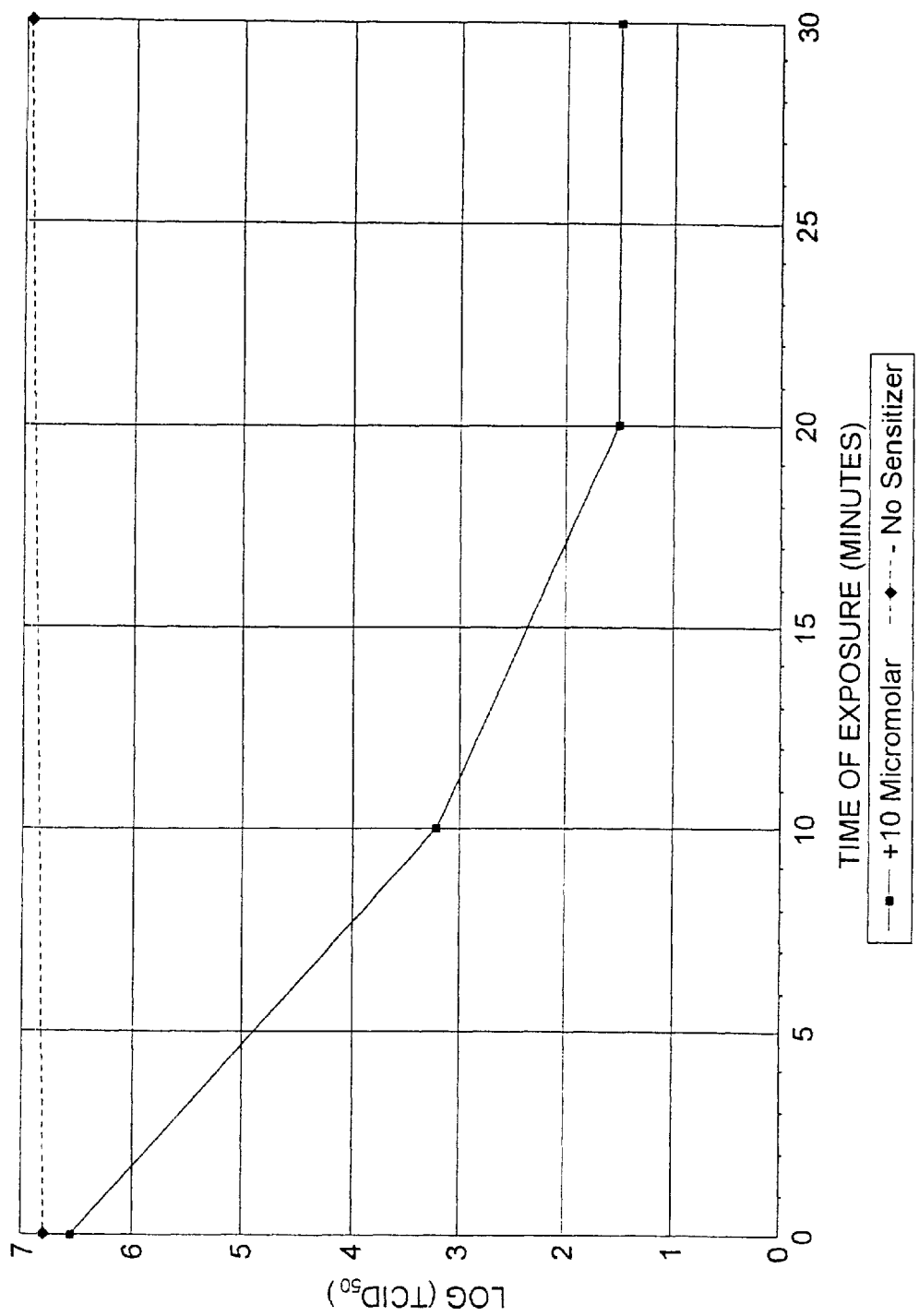
FIG. 18 compares inactivation results with and without sensitizer of vaccinia virus at varying irradiation times.

Samples of platelet concentrate in Isolyte S media 30:70, with and without 10 M 7,8 dimethyl-10-ribityl-isoalloxazine were spiked with vaccinia virus and irradiated at 60 J/cm$^2$ with 50:50 visible:UV light for varying periods of time and inactivation results compared as shown in FIG. 18.

Example 18

Figure 19:
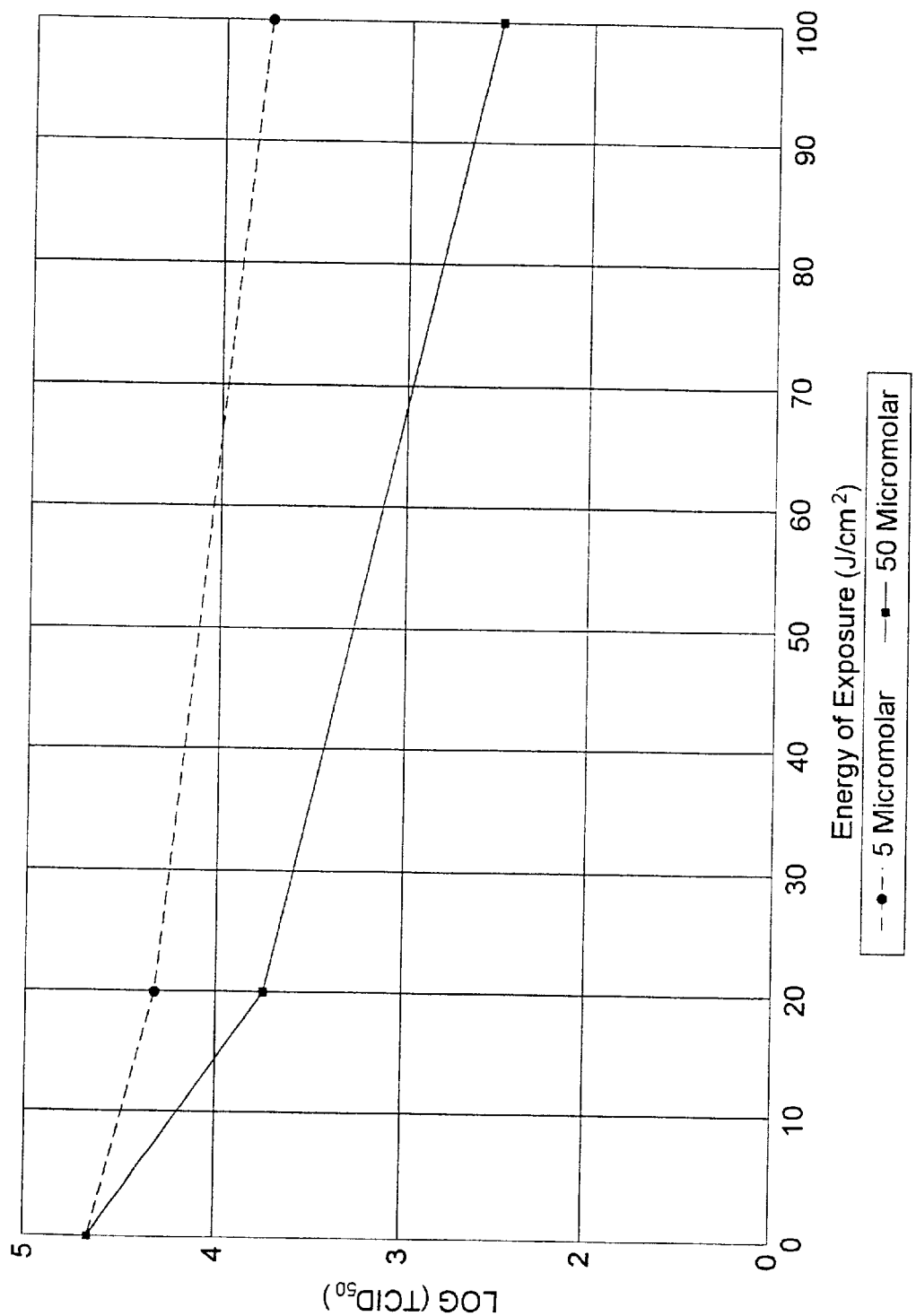
FIG. 19 compares inactivation of extracellular HIV-1 at 5 and 50 $\mu$M of photosensitizer and varying irradiation energies.

To samples of platelet concentrate as described in Example 6 were added 5 M or 50 M 7,8-dimethyl-10-ribityl-isoalloxazine. Samples were spiked with HIV 1. Using the cuvette flow cell shown in FIG. 5, samples were irradiated with 50:50 visible:UV light at varying energies using an EFOS light system. Inactivation results are shown in FIG. 19.

Example 19

Figure 20:
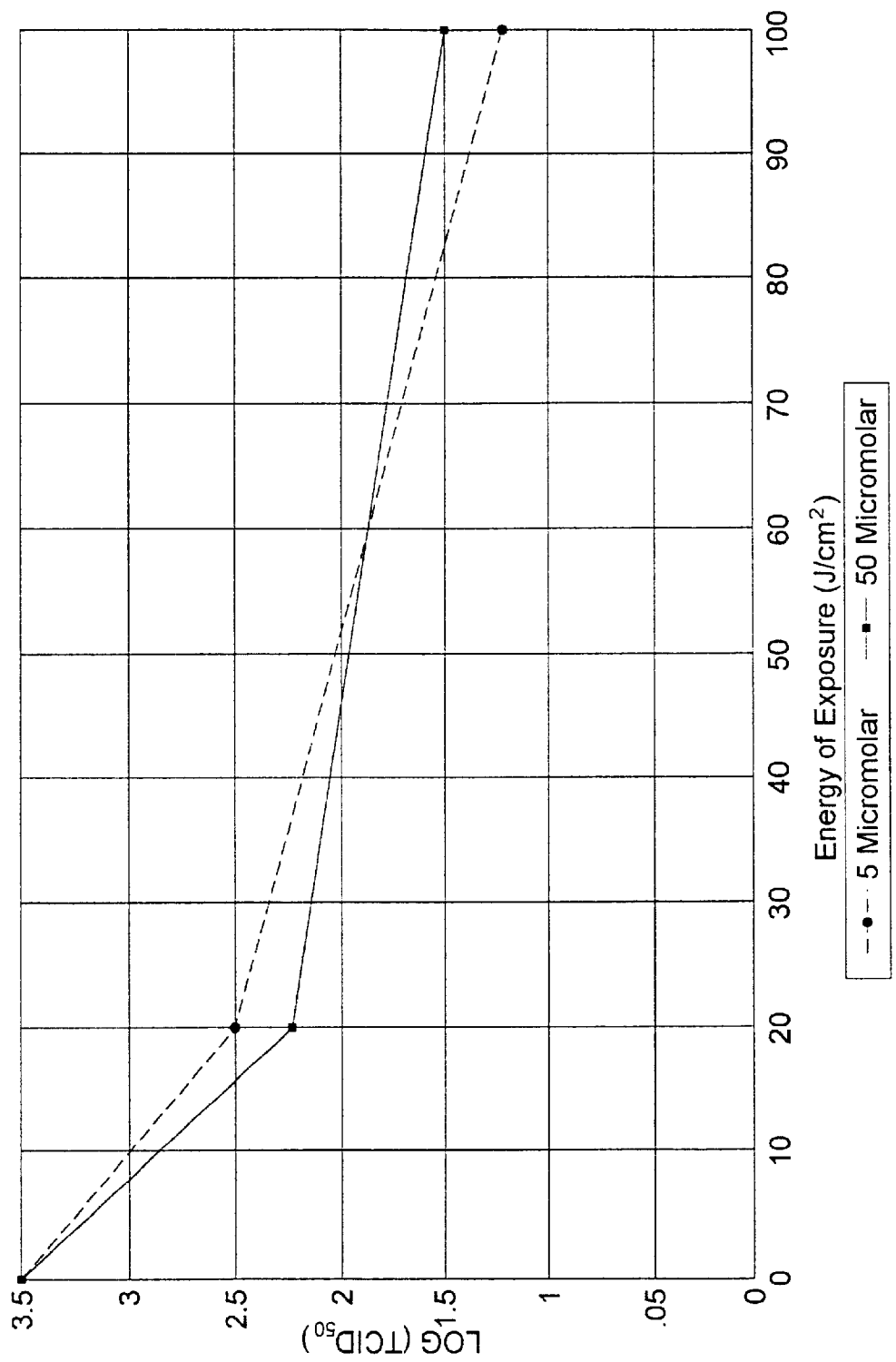
FIG. 20 compares inactivation of intracellular HIV-1 at 5 and 50 $\mu$M of photosensitizer and varying irradiation energies.

HIV-infected ACH-2 cells were added to samples of platelet concentrate described in Example 8. 5 or 50 $\mu$M of 7,8-dimethyl-10-ribityl-isoalloxazine were added to the samples. The protocol of Example 18 was followed, and inactivation results are shown in FIG. 20. The presence of HIV was assayed by its cytopathic effect on test cells.

Example 20

Figure 21:
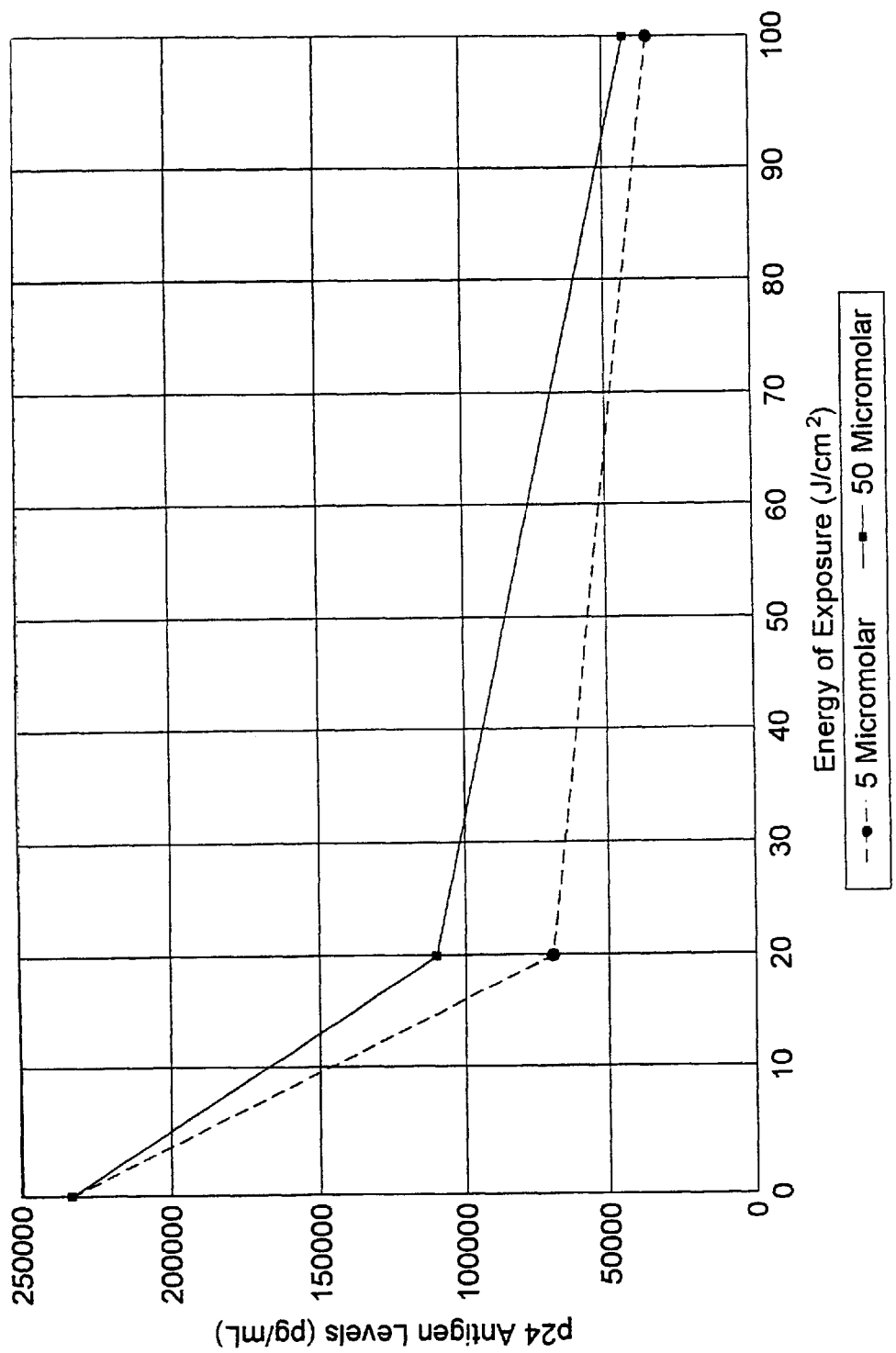
FIG. 21 compares inactivation of intracellular HIV-1 at 5 and 50 $\mu$M of photosensitizer and varying irradiation energies, using p24 antigen levels.

The protocol of Example 19 was followed and the presence of HIV assayed by quantifying the level of P24 antigen production. Inactivation results are show in FIG. 21.

Example 21

Figure 22:
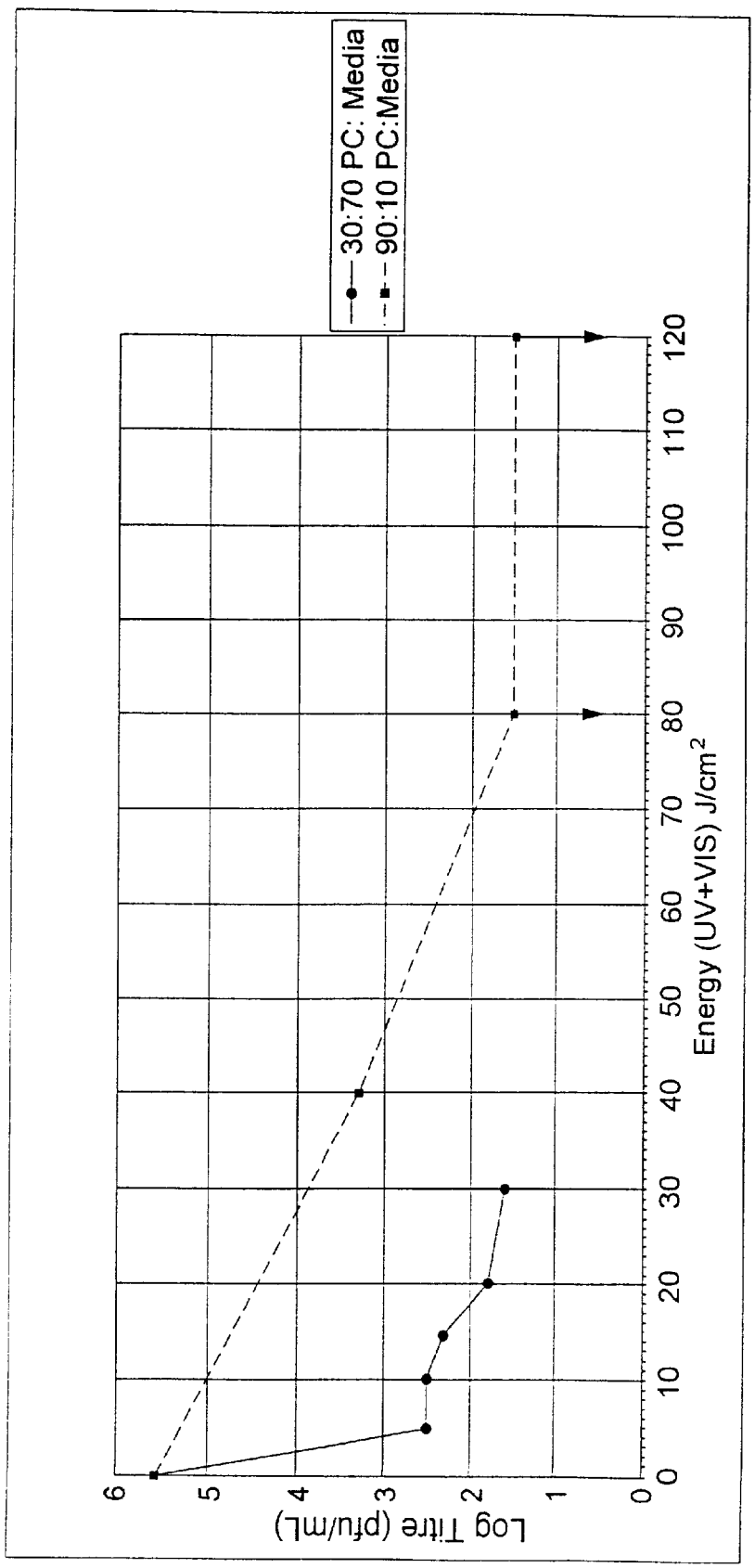
FIG. 22 shows inactivation of HSV-II at varying irradiation levels using platelet concentrate and platelet concentrate in media containing platelet additive solution with ascorbate.

To samples of platelet concentrate as described in Example 6 and media containing 30% platelet concentrate and 70% PASIIITM media were added 6 mM ascorbate and 14 $\mu$M 7,8-dimethyl-10-ribityl-isoalloxazine. Samples were spiked with HSV-II. Inactivation results are show in FIG. 22 and Table 5.

TABLE 5

| Time (Minutes) | Energy (UV+VIS) J/cm$^2$ | 30:70 PC:Media log virus titre | Energy (UV+VIS) J/cm$^2$ | 90:10 PC:Media log virus titre |
|---|---|---|---|---|
| 0.0 | 0 | 5.6 | 0 | 5.6 |
| 1.5 | 5 | 2.5 | 40 | 3.3 |
| 3.0 | 10 | 2.5 | 80 | 1.5 |
|  |  |  |  | No Detectable Virus |
| 4.5 | 15 | 2.3 | 120 | 1.5 |
|  |  |  |  | No Detectable Virus |
| 6.0 | 20 | 1.8 |  |  |
| 9.0 | 30 | 1.6 |  |  |
| 12.0 | 40 |  |  |  |
| 24.0 | 80 |  |  |  |
| 36.0 | 120 |  |  |  |

Example 22

This example compares novel blood component additive solutions for addition to platelets separated from whole blood. Six commercially available solutions were used: PAS II, PSMI-pH, PlasmaLyte A, SetoSol, PAS III, and PAS. To each known solution was added an effective amount of an endogenous photosensitizer, 7,8-dimethyl-10-ribityl isoalloxazine. The photosensitizer may be present in the various solutions at any desired concentration from about 1 $\mu$M up to the solubility of the photosensitizer in the fluid, or dry medium, and preferably about 10 $\mu$M. For 7,8-dimethyl-10-ribityl isoalloxazine a concentration range between about 1 $\mu$M and about 160 $\mu$M is preferred, preferably about 10 $\mu$M. The composition of each solution is shown in Table 6 below, and varies in the amount of blood component additives present. The blood additive components may be in a physiological solution, as well as a dry medium adapted to be mixed with a solvent, including tablet, pill or capsule form.

TABLE 6

| Blood Component Additive | Platelet Storage Solution | | | | | |
|---|---|---|---|---|---|---|
|  | PSS 1 | PSS 2 | PSS 3 | PSS 4 | PSS 5 | PSS 6 |
| KCl (mM) |  | 5.0 | 5.0 | 5.0 | 5.1 |  |
| CaCl$_2$ (mM) |  |  |  |  | 1.7 |  |
| MgCl$_2$ (mM) |  |  | 3.0 | 3.0 |  |  |
| MgSO$_4$ (mM) |  |  |  |  | 0.8 |  |
| sodium citrate (mM) | 10.0 | 23.0 | 23.0 | 17.0 | 15.2 | 12.3 |
| citric acid (mM) |  |  |  |  | 2.7 |  |
| NaHCO$_3$ (mM) |  |  |  |  | 35.0 |  |
| Na$_2$HPO$_4$ (mM) |  | 25.0 |  | 25.0 | 2.1 | 28.0 |
| sodium acetate (mM) | 30.0 |  | 27.0 | 23.0 |  | 42.0 |
| sodium gluconate (mM) |  |  | 23.0 |  |  |  |
| glucose (mM) |  |  |  |  | 23.5 | 38.5 |
| maltose (mM) |  |  |  |  | 28.8 |  |
| 7,8-dimethyl-10-ribityl isoalloxazine ($\mu$M) | 10.0 | 10.0 | 10.0 | 10.0 | 10.0 | 10.0 |

In Example 22, the platelet storage solution PSS 1 comprises a physiological saline solution, tri-sodium citrate at a concentration of approximately about 10 mM, sodium acetate at a concentration of approximately about 30 mM, and 7,8-dimethyl-10-ribityl isoalloxazine at a concentration of about 10 $\mu$M.

In Example 22, the platelet storage solution PSS 2 comprises a physiological saline solution, potassium chloride at a concentration of approximately about 5 mM, tri-sodium citrate at a concentration of approximately about 23 mM, a mixture of monosodium phosphate and dibasic sodium phosphate at a concentration of approximately about 25 mM, and 7,8-dimethyl-10-ribityl isoalloxazine at a concentration of about 10 μM.

In Example 22, the platelet storage solution PSS 3 comprises a physiological saline solution, potassium chloride at a concentration of approximately about 5 mM, magnesium chloride at a concentration of approximately about 3 mM, tri-sodium citrate at a concentration of approximately about 23 mM, sodium acetate at a concentration of approximately about 27 mM, sodium gluconate at a concentration of approximately about 23 mM, and 7,8-dimethyl-10-ribityl isoalloxazine at a concentration of about 10 μM.

In Example 22, the platelet storage solution PSS 4 comprises a physiological saline solution, potassium chloride at a concentration of approximately about 5 mM, magnesium chloride at a concentration of approximately about 3 mM, tri-sodium citrate at a concentration of approximately about 17 mM, sodium phosphate at a concentration of approximately about 25 mM, sodium acetate at a concentration of approximately about 23 mM, glucose at a concentration of approximately about 23.5 mM, maltose at a concentration of approximately about 28.8 mM, and 7,8-dimethyl-10-ribityl isoalloxazine at a concentration of about 10 μM.

In Example 22, the platelet storage solution PSS 5 comprises a physiological saline solution, potassium chloride at a concentration of approximately about 5.1 mM, calcium chloride at a concentration of approximately about 1.7 mM, magnesium sulfate at a concentration of approximately about 0.8 mM, tri-sodium citrate at a concentration of approximately about 15.2 mM, citric acid at a concentration of approximately about 2.7 mM, sodium bicarbonate at a concentration of approximately about 35 mM, sodium phosphate at a concentration of approximately about 2.1 mM, glucose at a concentration of approximately about 38.5 mM, and 7,8-dimethyl-10-ribityl isoalloxazine at a concentration of about 10 μM.

In Example 22, the platelet storage solution PSS 6 comprises a physiological saline solution, tri-sodium citrate at a concentration of approximately about 12.3 mM, sodium phosphate at a concentration of approximately about 28 mM, sodium acetate at a concentration of approximately about 42 mM, and 7,8-dimethyl-10-ribityl isoalloxazine at a concentration of about 10 μM.

In an aspect of this embodiment, physiologic saline may be replaced with a solvent comprising water and an effective amount of sodium chloride.

In this embodiment, the blood additive solution would comprise a commercially available product for example PAS II or T-Sol (which has the same ingredients as PAS II) and an effective amount of a nutrient such as glucose, an enhancer such as phosphate and 7,8-dimethyl-10-ribityl isoalloxazine in a pill or a dry medium form.

Example 23

This example compares novel blood additive solutions including an effective amount of 7,8-dimethyl-10-ribityl isoalloxazine in a liquid, pill or dry medium form. PSS 7, PSS 8 and PSS 9 are examples of such blood additive solutions set forth in Table 7 below.

TABLE 7

| | Platelet Storage Solution | | |
|---|---|---|---|
| Blood Component Additive | PSS 7 | PSS 8 | PSS 9 |
| NaCl (mM) | 115.0 | 78.3 | 68.5 |
| potassium chloride (mM) | | 5.7 | 5.0 |
| $MgCl_2$ (mM) | | 1.7 | 1.5 |
| sodium citrate (mM) | 10.0 | | |
| sodium phosphate (monobasic) | 6.2 | 5.4 | 8.5 |
| sodium phosphate (dibasic) | 19.8 | 24.6 | 21.5 |
| sodium acetate (mM) | 30.0 | 34.3 | 30.0 |
| 7,8-dimethyl-10-ribityl isoalloxazine (μM) | 14.0 | variable | 14.0 |

As described in Table 7, PSS 7 was prepared in RODI water and comprises sodium chloride at a concentration of approximately 115 mM, sodium citrate at a concentration of approximately 10.0 mM, sodium phosphate (monobasic) at a concentration of approximately 6.2 mM, sodium phosphate (dibasic) at a concentration of approximately 19.8 mM, sodium acetate at a concentration of approximately 30.0 mM, and 7,8-dimethyl-10-ribityl isoalloxazine at a concentration of approximately 14.0 μM. It has a pH of 7.2.

PSS 8 was prepared in RODI water and comprises sodium chloride at a concentration of approximately 78.3 mM, potassium chloride at a concentration of approximately 5.7 mM, magnesium chloride at a concentration of approximately 1.7 mM, sodium phosphate (monobasic) at a concentration of approximately 5.4 mM, sodium phosphate (dibasic) at a concentration of approximately 24.6 mM, sodium acetate at a concentration of approximately 34.3 mM, and a variable concentration of 7,8-dimethyl-10-ribityl isoalloxazine. It has a pH of 7.4, and an osmolarity of 297 mmol/kg.

PSS 9 was prepared in RODI water and comprises sodium chloride at a concentration of approximately 68.5 mM, potassium chloride at a concentration of approximately 5.0 mM, magnesium chloride at a concentration of approximately 1.5 mM, sodium phosphate (monobasic) at a concentration of approximately 8.5 mM, sodium phosphate (dibasic) at a concentration of approximately 21.5 mM, sodium acetate at a concentration of approximately 30.0 mM, and 7,8-dimethyl-10-ribityl isoalloxazine at a concentration of approximately 14.0 μM. It has a pH of 7.2, and an osmolarity of 305 mmol/kg.

It is understood that in PSS 7, PSS 8 and PSS 9 the RODI water and sodium chloride can be replaced with a saline solution.

It is also contemplated that a platelet additive solution in accordance with this invention can comprise 7,8-dimethyl-10-ribityl isoalloxazine and ascorbate.

Example 24

In this example, seven day storage of platelets is compared and evaluated. The platelets were collected using the apparatus of FIG. 1. The collected platelets had about 40% retained plasma. Additive constituents of citrate, bicarbonate and glucose, along with 7,8-dimethyl-10-ribityl isoalloxazine were mixed as described above and then added to the collected platelets prior to irradiation in accordance with the apparatus illustrated in FIG. 4. The constituent concentrations in the examples described in Tables 8–14 below were 8 μM of 7,8-dimethyl-10-ribityl isoalloxazine, approximately 65 mM of bicarbonate, and between 5.1–8.2 mM of citrate. For samples 5B and 7B, glucose was included in a concentration of 36 mM. For samples 6B and 8B, glucose was included in a concentration of 52 mM. Samples 5B and 6B were irradiated with light in the ultraviolet range having an intensity of 25 J/cm². Samples 7B and 8B were irradiated with a mixture of light from ultraviolet and visible sources having an intensity of 25 J/cm².

Table 8 indicates glucose consumption as a function of storage time (0, 1, 3, 6, and 7 days). The data indicates that, although glucose decreases over time, there is still residual glucose at the end of the seven day storage period.

TABLE 8

| | GLUCOSE (mmol/L) | | | | |
|---|---|---|---|---|---|
| | 0 | 1 | 3 | 6 | 7 |
| 5B | 41.9 | 34.3 | 27.4 | 18.8 | 17.4 |
| 6B | 51.1 | 45.9 | 39.1 | 28.3 | 29.9 |
| 7B | 39.9 | 36.6 | 31.3 | 20.8 | 19.9 |
| 8B | 51.3 | 49.7 | 43.0 | 32.6 | 33.7 |
| mean | 46.1 | 41.6 | 35.2 | 25.1 | 25.2 |
| SD | 6.0 | 7.4 | 7.1 | 6.4 | 7.8 |
| min | 39.9 | 34.3 | 27.4 | 18.8 | 17.4 |
| max | 51.3 | 49.7 | 43.0 | 32.6 | 33.7 |

Table 9 indicates the pH of the stored platelets as a function of time (0, 1, 3, 6, and 7 days). As can be seen from the data, the pH remains substantially the same.

TABLE 9

| | pH | | | | |
|---|---|---|---|---|---|
| | 0 | 1 | 3 | 6 | 7 |
| 5B | 7.6 | 7.5 | 7.4 | 7.4 | 7.4 |
| 6B | 7.6 | 7.5 | 7.4 | 7.3 | 7.3 |
| 7B | 7.7 | 7.6 | 7.6 | 7.6 | 7.5 |
| 8B | 7.7 | 7.6 | 7.6 | 7.6 | 7.6 |
| mean | 7.6 | 7.5 | 7.5 | 7.5 | 7.4 |
| SD | 0.0 | 0.1 | 0.1 | 0.1 | 0.1 |
| min | 7.6 | 7.5 | 7.4 | 7.3 | 7.3 |
| max | 7.7 | 7.6 | 7.6 | 7.6 | 7.6 |

Table 10 indicates the oxygen production over time (0, 1, 3, 6, and 7 days). After an initial increase, the oxygen production appears to remain stable.

TABLE 10

| | pO2 (mmHg) | | | | |
|---|---|---|---|---|---|
| | 0 | 1 | 3 | 6 | 7 |
| 5B | 109 | 140 | 132 | 141 | 134 |
| 6B | 109 | 140 | 132 | 141 | 133 |
| 7B | 113 | 136 | 125 | 135 | 128 |
| 8B | 113 | 132 | 126 | 141 | 126 |
| mean | 111.0 | 137.0 | 128.8 | 139.5 | 130.3 |
| SD | 2.3 | 3.8 | 3.8 | 3.0 | 3.9 |
| min | 109 | 132 | 125 | 135 | 126 |
| max | 113 | 140 | 132 | 141 | 134 |

Table 11 indicates the carbon dioxide production over time (0, 1, 3, 6, and 7 days). The data shows that carbon dioxide production decreases over time.

TABLE 11

| | pCO2 (mmHg) | | | | |
|---|---|---|---|---|---|
| | 0 | 1 | 3 | 6 | 7 |
| 5B | 63 | 74 | 47 | 22 | 16 |
| 6B | 69 | 74 | 49 | 22 | 16 |
| 7B | 58 | 61 | 44 | 26 | 21 |
| 8B | 58 | 61 | 42 | 23 | 19 |
| mean | 62.0 | 67.5 | 45.5 | 23.3 | 18.0 |
| SD | 5.2 | 75 | 3.1 | 1.9 | 2.4 |
| min | 58 | 61 | 42 | 22 | 16 |
| max | 69 | 74 | 49 | 26 | 21 |

Table 12 indicates the cell count of the stored platelets as a function of time (0, 1, 3, 6, and 7 days).

TABLE 12

| | Cell Count 10⁶/ml | | | | |
|---|---|---|---|---|---|
| | 0 | 1 | 3 | 6 | 7 |
| 5B | 761 | 624 | 668 | 598 | 557 |
| 6B | 729 | 645 | 648 | 624 | 610 |
| 7B | 786 | 703 | 664 | 601 | 568 |
| 8B | 762 | 667 | 628 | 586 | 554 |
| Mean | 759.5 | 659.8 | 652.0 | 602.3 | 572.3 |
| SD | 23.4 | 33.8 | 18.2 | 15.9 | 25.9 |
| min | 729 | 624 | 628 | 586 | 554 |
| max | 786 | 703 | 668 | 624 | 610 |

Table 13 indicates the hypertonic shock (HSR) response of the stored platelets over time (0, 1, 3, 6, and 7 days).

TABLE 13

| | HSR - % Reversal | | | | |
|---|---|---|---|---|---|
| | 0 | 1 | 3 | 6 | 7 |
| 5B | 33.3 | 24.0 | 25.0 | 32.1 | 13.3 |
| 6B | 41.2 | 31.8 | 23.7 | 36.0 | 15.4 |
| 7B | 52.6 | 34.8 | 34.3 | 72.2 | 30.8 |
| 8B | 55.0 | 40.0 | 34.3 | 61.9 | 26.3 |
| mean | 45.5 | 32.7 | 29.3 | 50.6 | 21.5 |
| SD | 10.1 | 6.7 | 5.8 | 19.6 | 8.4 |
| min | 33.3 | 24.0 | 23.7 | 32.1 | 13.3 |
| max | 55.0 | 40.0 | 34.3 | 72.2 | 30.8 |

Table 14 indicates the bicarbonate concentration as a function of time, (0, 1, 3, 6, and 7 days). As the data indicates, bicarbonate decreases over time with a small concentration remaining on the seventh day of the storage period.

TABLE 14

| | Bicarb mmol/L | | | |
|---|---|---|---|---|
| | 0 | 1 | 3 | 7 |
| 5B | 65.8 | 52.2 | 29.6 | 9.2 |
| 6B | 65.7 | 51.0 | 28.8 | 7.3 |
| 7B | 64.9 | 56.7 | 37.3 | 16.6 |
| 8B | 63.4 | 55.4 | 37.3 | 18.1 |
| mean | 64.9 | 53.9 | 33.2 | 12.8 |
| SD | 1.1 | 2.7 | 4.7 | 5.4 |
| min | 63.4 | 51.0 | 28.8 | 7.3 |
| max | 65.8 | 56.7 | 37.3 | 18.1 |

A preferred additive/storage solution for collected platelets having between 20–45% residual plasmas comprises bicarbonate as a buffer; glucose as a nutrient; and citrate as an additional anticoagulant. The preferred additive storage solution with the concentrations given in approximate amounts per liter is shown in Table 15.

TABLE 15

| CONSTITUENT | CONCENTRATION |
| --- | --- |
| glucose | 33–52 mM |
| sodium bicarbonate | 63–95 mM |
| citrate | 5.1–8.8 mM |

It is understood that the above storage solution can be used to store platelets even when a decontamination process is not needed or contemplated.

If it is desired to decontaminate the blood product through the use of a photosensitizer, it is contemplated that an endogenous alloxazine be added in an effective amount as described above. The solution described in Table 16 is a solution suitable for viral decontamination as well as for platelet storage; the concentrations are given in approximate amounts per liter.

TABLE 16

| CONSTITUENT | CONCENTRATION |
| --- | --- |
| glucose | 33–52 mM |
| sodium bicarbonate | 63–95 mM |
| sodium citrate | 5.1–8.8 mM |
| 7,8-dimethyl-10-ribityl isoalloxazine | 8–50 mM |

With all the solutions set forth above it is understood that all concentrations are approximate and can be varied as will be readily understood by one skilled in the art. Also, from the concentrations given above the gram weights can be readily determined if the photosensitizer or additive constituents are to be added in dry form.

It will be readily understood by those skilled in the art that the foregoing description has been for purposes of illustration only and that a number of changes may be made without departing from the scope of the invention. For example, other photosensitizers than those mentioned may be used, preferably photosensitizers which bind to nucleic acid and thereby keep it from replicating, and more preferably those which are not toxic and do not have toxic breakdown products. In addition, equivalent structures to those described herein for constructing a flow-through system for decontamination of fluids using photosensitizers may be readily devised without undue experimentation by those skilled in the art following the teachings hereof.

What is claimed is:

1. A fluid to be used in the decontamination treatment of and the storage of blood or blood components comprising:

a nutrient;

7,8-dimethyl-10-ribityl isoalloxazine;

a buffer; and an anticoagulant wherein the nutrient comprises glucose in a concentration between 33–55 $\mu$M, wherein the buffer comprises bicarbonate in a concentration between 63–95 $\mu$M, and wherein the anticoagulant comprises citrate in a concentration between 5.1–8.8 $\mu$M.

2. The fluid of claim 1 wherein the nutrient and 7,8-dimethyl-10-ribityl isoalloxazine are combined to form a first aqueous mixture;

the buffer and anticoagulant are combined to form a second aqueous mixture; and the first and second mixtures are combined to form the fluid.

* * * * *

UNITED STATES PATENT AND TRADEMARK OFFICE
CERTIFICATE OF CORRECTION

PATENT NO. : 6,548,241 B1
APPLICATION NO. : 09/725426
DATED : April 15, 2003
INVENTOR(S) : Laura M. McBurney et al.

It is certified that error appears in the above-identified patent and that said Letters Patent is hereby corrected as shown below:

Column 32, line 23, change ...33-55 µM,... to ...33-55 mM,..

Column 32, line 24, change ...63-95 µM,... to ...63-95 mM...

Column 32, line 26, change ...5.1-8.8 µM.... To ...5.1-8.8 mM...

Signed and Sealed this

Twenty-second Day of August, 2006

JON W. DUDAS
*Director of the United States Patent and Trademark Office*